US008178320B2

(12) United States Patent
Shimizu et al.

(10) Patent No.: US 8,178,320 B2
(45) Date of Patent: May 15, 2012

(54) ARTIFICIAL ANTIBODY LIBRARY WITH SUPER-REPERTORY

(75) Inventors: Nobuyoshi Shimizu, Tokyo (JP);
Atsushi Takayanagi, Tokyo (JP);
Michiyo Okui, Tokyo (JP)

(73) Assignee: Keio University (JP)

( * ) Notice: Subject to any disclaimer, the term of this patent is extended or adjusted under 35 U.S.C. 154(b) by 555 days.

(21) Appl. No.: 10/496,349

(22) PCT Filed: Nov. 22, 2002

(86) PCT No.: PCT/JP02/12236
§ 371 (c)(1),
(2), (4) Date: Sep. 1, 2004

(87) PCT Pub. No.: WO03/044198

PCT Pub. Date: May 30, 2003

(65) Prior Publication Data
US 2006/0057632 A1 Mar. 16, 2006

(30) Foreign Application Priority Data

Nov. 22, 2001 (JP) ................................ 2001-358602

(51) Int. Cl.
*C12P 21/04* (2006.01)
*C12P 21/08* (2006.01)
*C12Q 1/70* (2006.01)
*C12N 15/00* (2006.01)
*A61K 39/00* (2006.01)
*A61K 39/395* (2006.01)

(52) U.S. Cl. ..... 435/69.6; 435/5; 435/320.1; 530/387.3; 424/135.1

(58) Field of Classification Search .................. None
See application file for complete search history.

(56) References Cited

U.S. PATENT DOCUMENTS

| 5,565,332 | A | * | 10/1996 | Hoogenboom et al. | ..... 435/69.1 |
| 5,855,885 | A | * | 1/1999 | Smith et al. | ........................ 506/4 |
| 6,662,113 | B1 | | 12/2003 | Shimizu et al. | |

FOREIGN PATENT DOCUMENTS

| EP | 0 976 836 A1 | 2/2000 |
| EP | 1092768 A1 * | 4/2001 |
| EP | 1 227 147 A2 | 7/2002 |
| JP | 10-507341 | 7/1998 |
| JP | 11-196880 | 7/1999 |
| JP | 201-516215 | 9/2001 |
| WO | WO 95/27045 | 10/1995 |
| WO | WO 96/40724 | 12/1996 |
| WO | WO 98/41622 | 9/1998 |
| WO | WO 99/31270 | 6/1999 |
| WO | WO 0031246 A2 * | 6/2000 |
| WO | WO 01/05961 A1 | 1/2001 |
| WO | WO 01/75091 A2 | 10/2001 |
| WO | WO 02/04629 A2 | 1/2002 |
| WO | WO 02/40685 A2 | 5/2002 |

OTHER PUBLICATIONS

Tsurushita, N., Fu, H., and C. Warren. Phage display vectors for in vivo recombination of immunoglobin heavy and light chain genes to make large combinatorial libraries. Gene 172:59-63 1996.*
Gavilondo, J.V., and Larrick, J.W. Antibody engineering at the millennium. 2000. Biotechniques, vol. 29, No. 1, pp. 128-145. (renumbered sequentially pp. 1-19).*
Knudsen, C.R., and Clark, B.F.C. Expression Systems 1999 in Encyclopedia of Molecular Biology, T.E. Creighton ed. John Wiley and Sons, Inc. vol. 2, pp. 883-886.*
Rader, C., Cheresh, D.A., and Barbas, C.F. A phage display approach for rapid antibody humanization: designed combinatorial V gene libraries. 1998. Proceedings of the National Academy of Sciences, vol. 95, pp. 8910-8915.*
Wilson, A.K. Polymerase Chain Reaction 1999 in Encyclopedia of Molecular Biology, T.E. Creighton ed. John Wiley and Sons, Inc. vol. 3, pp. 1903-1908.*
Zahra, D.G., Vancov, T., Dunn, J.M., Hawkins, N. J., and Ward, R.L. Selectable in-vivo recombination to increase antibody library size—an improved phage display vector system. Gene. 1999, vol. 227, pp. 49-54.*
Lewin, B. Genes IV. 1990. Oxford Univeristy Press, p. 810.*
Buck et al., Biotechniques, 1999, 27(3): 528-536.*
Scott et al., Gene Therapy, 2000, 7:1121-1125.*
Alexander, Ribosomes, 1999, p. 277.*
Nakamoto, BBRC, 2006, 341:675-678.*
Araki, Kimi et al., "Targeted integration of DNA using mutant *lox* sites in embryonic stem cells," Nucleic Acids Research, 1997, vol. 25, No. 4, 868-872.
Benhar, Itai et al., "Highly Efficient Selection of Phage Antibodies Mediated by Display of Antigen as Lpp-OmpÅ Fusions on Live Bacteria," J. Mol. Biol. (2000) 301, 893-904.
Biard-Piechaczyk, Martine et al., "Human single-chain Fv fragments from a combinatorial library using the loxP-Cre recombination system," Human Aritibodies 9 (1999) 67-77.
Geoffroy, Frédérique et al., "A new phage display system to construct multicombinatorial libraries of very large antibody repertoires," Gene, 151 (1994) 109-113.
de Kruif, John et al., "Selection and Application of Human Single Chain Fv Antibody Fragments from a Semi-synthetic Phage Antibody Display Library with Designed CDR3 Regions," J. Mol. Biol. (1995) 248, 97-105.
Kahn, Patricia, "From Genome to Proteome: Looking at a Cell's Proteins," Science, New Series, vol. 270, No. 5235 (Oct. 20, 1995), 369-370.
Poul, Marle-Alix et al., "Targeted Gene Delivery to Mammalian Cells by Filamentous Bacteriophage," J. Mol. Biol. (1999) 288, 203-211.

(Continued)

*Primary Examiner* — Anne M. Gussow
(74) *Attorney, Agent, or Firm* — Barnes & Thornburg LLP

(57) ABSTRACT

An artificial antibody library with a super-repertory ($10^{11}$ or more) is constructed by: using a cDNA library as a template, amplifying a fragment containing the CDR1 and CDR2s regions of the VH or VL region of immunoglobulin gene and a fragment containing the CDR3 region each by the PCR method; integrating the VH library and the VL library, which are little contaminated with unexpressionable repertory and have high safety, into an non-expression vector; transferring it into a host; and then shuffling the VH region in the VH library with the VL region in the VL library.

28 Claims, 17 Drawing Sheets

OTHER PUBLICATIONS

Ringrose, Leonie et al., "Comparative Kinetic Analysis of FLP and Cre Recombinases: Mathematical Models for DNA Binding and Recombination," J. Mol. Biol. (1998) 284, 363-384.

Sblattero, Daniele et al., "Exploiting recombination in single bacteria to make large phage antibody libraries," Nature Biotechnology, vol. 18, Jan. 2000, 75-80.

Scott, Jamie K. et al., "Searching for Peptide Ligands with an Epitope Library," Science, New Series, vol. 249, No. 4967 (Jul. 27, 1990), 386-390.

Siegel, Robert W. et al., "Using an in vivo phagemid system to identify non-compatible *loxP* sequences," FEBS Letters 505 (2001) 467-473.

Siegel, Robert W. et al., "Recombinatorial Cloning Using Heterologous Lox Sites," Genome Research 14: 1119-1129, 2004.

Smith, George P. et al., "Libraries of Peptides and Proteins Displayed on Filamentous Phage," Methods in Enzymology, vol. 217, 228-257, 1993.

Takayanagi, Atsush et al., "Preparation of a Phage-display Human Single Chain Antibody Library by Double Shuffling Method" (Abstract only), Aug. 2002 75th p. 870, 3P-208.

Tsurushita, Naoya et al., "Phage display vectors for in vivo recombination of immunoglobulin heavy and light chain genes to make large combinatorial libraries," Gene, 172 (1996), 59-63.

Van Den Beucken et al., "Building Novel Binding Ligands to B7.1 and B7.2 Based on Human Antibody Single Variable Light Chain Domains," J. Mol. Biol. (2001) 310, 591-601.

Waterhouse, Peter et al., "Combinatorial infection and in vivo recombination: a strategy for making large phage antibody repertoires," Nucleic Acids Research, 1993. vol. 21, No. 9, 2265-2266.

Weaver-Feldhaus, Jane M. et al.. "Yeast mating for combinatorial Fab library generation and surface display," FEDS Letters 564 (2004) 24-34.

Zacchi, Paola et al., "Selecting Open Reading Frames From DNA," Genome Research 13:980-990, 2003.

Zahra, David G. et al., "Selectable in-vivo recombination to increase antibody library size-an improved phage display vector system," Gene 227 (1999) 49-54.

Tanha, Jamshid et al., "Optimal Design Features of Camelized Human Single-domain Antibody Libraries," The Journal of Biological Chemistry, vol. 276, No. 27, Issue of Jul. 6, 2001, pp. 24774-24780.

Kasai, Shigenobu et al.; "Immunoassay of the MRSA-Related Toxic Protein, Leukocidin, with Scanning Electrochemical Microscopy" Anal. Chem. 72(23): pp. 5761-5765 (2000).

Lam, Kit S. et al., "A One-Bead One-Peptide Combinatorial Library Method for B-Cell Epitope Mapping" Methods: A Companion to Methods in Enzymology 9: pp. 482-493 (1996).

Nishihara, Tohru et al., "A T7 promoter vector with a transcriptional terminator for stringent expression of foreign genes" Gene 145: pp. 145-146 (1994).

"Construction of a Library of Perfect Human Artificial Antibodies (AIMS) Using Phase Display System and Examination of its Clinical Application in which Molecular Target is Antiogenesis", Journal of Japanese Society of Clinical Oncology, vol. 34, No. 2, p. 93, published Sep. 20, 1999.

"Preparation of a Phase-display Human Single Chain Antibody Library by Double Shuffling Method", Seikagaku, vol. 74, No. 8, p. 870, published Aug. 25, 2002.

* cited by examiner existence of immunoglobulin gene for each clone 1 2 3 4 5 6 7 8 9 10 11 12 13 14 15 16 17 18 19 20 21 22 23 24 25 26 27 28 29 30 31 32

| VH gene | | Vκ gene | | Vλ gene | |
|---|---|---|---|---|---|
| VH 1-8 | 1 | A27 | 13 | V 1-4 | 3 |
| VH 1-24 | 2 | L2 | 2 | V 1-16 | 1 |
| VH 1-46 | 3 | L6 | 1 | V 1-17 | 1 |
| VH 1-58 | 2 | L8 | 1 | V 1-20 | 3 |
| VH 1-69 | 2 | O8 | 2 | V 1-22 | 1 |
| VH 2-5 | 3 | | | V 2-3 | 1 |
| VH 3-30 | 1 | | | | |
| VH 3-33 | 2 | | | | |
| VH 3-73 | 1 | | | | |
| VH 4-28 | 1 | | | | |
| VH 4-34 | 3 | | | | |
| VH 6-1 | 6 | | | | |
| total | 27 | | 17 | | 10 | variation of immunoglobulin genes (genome-derived)

FIG.15

```
              <------FWR1-------->   <---CDR1--->   <-----FWR2---->   <--CDR2>
TM1 scFv      ETTLTQSPSSLSASVGDRVTIC RTSQTINNYLN    WYQQKPGKAPKVLIF   GASRLQS
O2(kappa)     DIQM................. .A..S.SS...    ...........L..Y   A..S...

<------FWR3---------->                <--CDR3-->        <----J---->
              GVPSRFSGSGSGTHFTLTITSLQPEDVATYYC      QQSYGTPY          TFGQGTKVEIK
              .............D...S...F.......        .....S..

linker        VDITSYNVYYTKLSLE

<------FWR1---------->                <CR1>             <-----FWR2---->   <-----CDR2------>
              QVQLQQWGAGLLKPSETLSLTCAIYNGSFG        GYYWN             WIRQPPGKGLEWIG    EINQRESTNFNPSFKS
VH4-34        ..................V.G...S            ....S             ..............    ..HSG....Y....L..

<------FWR3----------->               <-----CDR3----------->             <----J---->
              RVTMSVDTSNNQFSLRLSSLTAADTAVYFCAR      GLYYDTTGFFDAFA                     VWGQGTTVTVS
              ...I.....K....K...V........Y....

Vector        HLGLMGHHHHHH....
```

FIG.17

ARTIFICIAL ANTIBODY LIBRARY WITH SUPER-REPERTORY

CROSS-REFERENCE TO RELATED APPLICATIONS

This application is a U.S. national counterpart application of international application serial no. PCT/JP02/12236 filed Nov. 22, 2002, which claims priority to Japanese application serial no. 2001-358602 filed Nov. 22, 2001.

TECHNICAL FIELD

The present invention relates to categorized single chain antibody library free from problems such as the contamination of a repertory which cannot be expressed or instability of the library, antibody chips, and antibody filters; and the screening for antigen-specific antibodies, epitope-specific antibodies, antibody-specific antigens, or ligands bound to antibodies, the analysis/evaluation of protein-protein interaction or DNA-protein interaction, and the diagnosis/therapeutic agents of various diseases, using the library, the chips and the filters.

BACKGROUND ART

An antibody molecule consists of two polypeptide chains, each of which has an H-chain and L-chain. It is known that each of the H- and L-chains comprises a sequence of domains consisting of about 110 amino acids each and that an L-chain comprises two domains (VL and CL) and an H-chain comprises four domains ($V_H$, $C_{H1}$, $C_{H2}$ and $C_{H3}$). The structural gene ($V_H$ gene) encoding a variable region of an H-chain comprises three gene fragments, i.e., V, D and J gene fragments, while the structural gene ($V_L$ gene) encoding an L-chain comprises two gene fragments, i.e., J and V gene fragments regardless of whether the L-chain belongs to a λ or κ chain. On such variable regions, an antigen-binding site responsible for the recognition of a specific antigen is formed. Immunoglobulin molecules are widely diversified in their primary structure, even when they are derived from the same animal species and belong to the same class, and particularly contain the hypervariable regions, whose diversity is remarkable. In a hypervariable region, complementarity-determining regions (CDRs), each of which has a 3D structure complementary to a specific antigen molecule and thus determines the specificity of the antibody, and framing regions (FRs), which support the 3D structure of the hypervariable region, are arranged in a mosaic fashion. It has been known that the hypervariable region formed on each of the H- and L-chains comprises three highly variable regions called CDR1, CDR2, and CDR3, which can specifically bind to various antigens as a result of the diversity of amino acid sequences of CDRs.

Usually, an antibody is made by a method of immunizing an animal with a foreign antigen. Accordingly, it has been thought that it is difficult to prepare a specific antibody with an animal against its own substance or a substance that is closely similar to it. Recently, a method for making antibodies using a phage antibody library has been established. This method is an application of displaying an antibody on the surface of phages by fusing an antibody to the coat protein of a filamentous phage. According to this method, a library having a wide variety of antibodies is made by amplifying the genes encoding antibody by PCR, and by displaying it on the phage particles. By this method it is possible to prepare antibodies against a human antigen. A screening method using a phage display library is called a phage display method and has been used for the identification of ligands that specifically bind to various receptors of cells or various antibodies. Many reports have been already published on how to prepare phage antibody libraries, immuno-tube methods using such a phage antibody library, and screening methods such as magnetic bead method (Science, 249:386-390(1990); Methods in Enzymology, 217:228-257(1993)).

Such an antibody library including an enormous repertory described above is an excellent technique that can save immunological operations and time for screening, can be widely applicable for the preparation of various antibodies, and simplify screening. However, an antibody library that has been prepared so far is problematic because of contamination of a repertory that cannot be expressed and instability. In an antibody library that has been prepared so far, amplification rate of individual clones are often varied, and thus it is difficult to maintain an enormous repertory. Methods for other library preparations were reported, by which a repertory involved in the production of antibodies in a spleen or bone marrow cells is used or random amino acid sequences are integrated in immunoglobulin genes to obtain a repertory with $10^{12}$ or more antibodies (see, for example, J. Molecular Biology, 248:97-105, 1995). With these methods, however, the contamination of a repertory which cannot be expressed, such as genes that encode non-functional antibodies, which have occurred by insertion of a translation termination codon or influence to high-order structures of antibody molecules, or instability of the library cannot be avoided.

On the other hand, VL-VH shuffling via *E. coli* in which shuffling is made in an sc Fv (single-chain Fragment variable) library to increase the size of its repertory, i.e. VH-gp3 fragments are shuffled (Nature Biotech., 18:75-80, 2000), preparation of a library of recombinant polynucleotides derived from single or double stranded parental DNA templates as various starting materials (PCT Japanese Translation Patent Publication No. 2001-516215), and method for producing catalytic antibodies that are displayed on phages comprising processes for preparing a library of DNA fragments encoding an antibody domain, inserting the domain-encoded fragments into a phage expression vector, and isolating the catalytic antibodies (PCT Japanese Translation Patent Publication No. 10-507341). However, there has never been reported a useful single-chain antibody library having a repertory of $10^{11}$ or more antibodies, for example, $10^{12}$ antibodies. In addition, no method has existed for selectively producing a single chain antibody comprising a VH and VL regions obtained by shuffling.

DISCLOSURE OF INVENTION

It is said that Human Genome Project will end soon thanks to the recent rapid progress in sequencing techniques. However, even when the genome of an organism is completely sequenced, genes, function of whose products can be inferred by search of homologous genes using databases, are very rare. Furthermore, many of the proteins which are expressed and functional in a cell are varied according to the variation of its expression level and post-translational modification by the condition of the cell. A set of proteins that exist at a given moment of life activity is proposed to be named a proteome based on the combination of PROTEin and genOME as a new concept (Kahn, P., Science, 270:360-370, 1995). Indeed, the variations have been analyzed, by understanding the total image of the proteome at one moment and comparing the image with the one at another moment. Such an attempt for investigating biological phenomena by analyzing dynamics of the proteomes at a large scale is called proteomics, which attracts attention as a post genome sequencing project. An epoch-making breakthrough is expected if the genome analyses that have accumulated the huge amount of knowledge are applied to the proteomics. The object of the present invention is to provide antibody libraries with a categorized repertory (list) with more than $10^{11}$ components, which are free from problems such as the contamination of a repertory which cannot be expressed or instability of the library and are useful for the screenings for antigen-specific antibodies, epitope-specific antibodies, antibody-specific antigens, or ligands bound to antibodies, the analysis/evaluation of protein-protein interaction or DNA-protein interaction, and diagnosis/therapeutic reagents of various diseases, antibody chips antibody filters, and antibody beads.

The present inventors had intensively studied proteomics based on genome analysis to find a method for obtaining a single chain antibody library with more than $10^{11}$ components, which will serve as a useful tool for proteomics, by amplifying separately the gene fragments comprising CDR1 and CDR2 regions of the immunoglobulin gene and those comprising CDR3 region using a cDNA library as a template with PCR, inserting into a non-expression vector a VH library whose titer is $10^6$ or more and a VL library whose titer is $10^5$ or more, both of which contain small amount of contamination of a repertory which cannot be expressed and are highly stable, introducing the recombinant vectors into a host, and shuffling the VH regions in the VH library and the VL regions in the VL library, and an antibody chip and filter using the library. This discovery led to the present invention.

Namely, the present invention provides the inventions described in the following Paragraphs (1) to (57).

1. A method for preparing a single chain antibody library comprising:
   step (a) for amplifying gene fragments including the CDR1 and CDR2 and the CDR3 region of the VH or VL region in an immunoglobulin gene by PCR using a cDNA library as a template;
   step (b) for shuffling gene fragments between gene fragments including the CDR1 and CDR2 regions and gene fragments including the CDR3 region in each of the VH and VL regions to produce thereby VH and VL libraries;
   step (c) for inserting the VH and VL libraries obtained at step (b) into two different non-expression vectors;
   step (d) for shuffling gene fragments between the VH region in the VH library and the VL region in the VL library by introducing both the VH library-incorporated non-expression vector and VL library-incorporated non-expression vector into a host; and
   step (e) for displaying a single chain antibody comprising VH and VL regions obtained by shuffling on the surface of a phage.

2. A method for preparing a single chain antibody library as described in Paragraph 1 wherein the cDNA library is a peripheral blood cDNA library, a spleen cDNA library or a bone narrow cDNA library.

3. A method for preparing a single chain antibody library as described in Paragraph 1 or 2 wherein the cDNA library is derived from human being or mouse.

4. A method for preparing a single chain antibody library as described in any one of Paragraphs 1 to 3 wherein PCR amplification is performed by using one or more of the primers whose nucleotide sequences are as represented in Seq. ID Nos. 1-48.

5. A method for preparing a single chain antibody library as described in Paragraph 1 in which step (a) comprises:
   substep (i) for amplifying gene fragments including the CDR1 and CDR2 regions and gene fragments including the CDR3 region in the VH region of the immunoglobulin gene using a human peripheral blood cDNA library and a human spleen cDNA library as template, the primers, one of which is selected from Seq. ID Nos. 1-7 and the other of which is Seq. ID No. 8 or 9, and the primers, one of which is Seq. ID No. 10 or 11 and the other of which is selected from Seq. ID No. 12-17, respectively;
   substep (ii) for amplifying gene fragments including the CDR1 and CDR2 regions and gene fragments including the CDR3 region of the Vκ region in the immunoglobulin gene by PCR using a human peripheral blood and a spleen cDNA library as template, and primers, one of which is selected from Seq. ID Nos. 18-21 and the other of which is Seq. ID No. 22 or 23, and primers, one of which is Seq. ID No. 24 or 25 and the other of which is selected from Seq. ID No. 26-29; and
   substep (iii) for amplifying gene fragments including the CDR1 and CDR2 regions and gene fragments including the CDR3 region of the Vλ region in the immunoglobulin gene using a human peripheral blood cDNA library or a spleen cDNA library as template, and the primers, one of which is selected from Seq. ID Nos. 30-38 and the other of which is selected from Seq. ID No. 39-42, and the primers, one of which is selected from Seq. ID No. 43-46 and the other of which is Seq. ID No. 47 or 48, respectively.

6. A method for preparing a single chain antibody library as described in Paragraph 5 in which step (b) further comprises:
   substep (i) for shuffling the gene fragments between gene fragments including CDR1 and CDR2 and gene fragments including CDR3 in the VH region by PCR using two primers, one of which is selected from Seq. ID Nos. 1-7 and the other of which is selected from Seq. ID Nos. 12-17;
   substep (ii) for shuffling the gene fragments between gene fragments including CDR1 and CDR2 and gene fragments including CDR3 in the Vκ region by PCR using two primers, one of which is selected from Seq. ID Nos. 18-21 and the other of which is selected from Seq. ID Nos. 26-29; and
   substep (iii) for shuffling the gene fragments between gene fragments including CDR1 and CDR2 and gene fragments including CDR3 in the Vλ region of an antibody by PCR using two primers, one of which is selected from Seq. ID Nos. 30-38 and the other of which is selected from Seq. ID No. 47 or 48.

7. A method for preparing a single chain antibody library as described in any one of Paragraphs 1 to 6 wherein a VH- and/or VL library obtained at step (b) contain a small amount of contamination of a repertory which cannot be expressed and highly stable.

8. A method for preparing a single chain antibody library as described in any one of Paragraphs 1 to 7 wherein the shuffling described in step (d) is performed by DNA recombination via recombinase.

9. A method for preparing a single chain antibody library as described in Paragraph 8 wherein the recombinase is recombinase Cre or FLP recombinase.

10. A method for preparing a single chain antibody library as described in any one of Paragraphs 1 to 9 wherein only single chain antibodies including VH and VL regions obtained by shuffling performed at step (d) are displayed on the surface of phage.

11. A method for preparing a single chain antibody library as described in any one of Paragraph 1 to 10 wherein two different non-expression vectors are a promoter-free vector and a SD sequence-free vector.

12. A method for preparing a single chain antibody library as described in any one of Paragraphs 1 to 10 wherein the two different non-expression vectors are a promoter-free vector and a vector that contains a transcription termination signal.

13. A method for preparing a single chain antibody library as described in any one of Paragraphs 1 to 12 wherein the two different non-expression vectors comprise a mutated reverse-oriented repeat sequence obtained by mutating a wild-type reverse-oriented repeat sequence recognized by recombinase.

14. A method for preparing a single chain antibody library as described in Paragraph 13 wherein the mutated reverse-oriented repeat sequence obtained by mutating a wild-type reverse-oriented repeat sequence recognized by recombinase is a mutated loxP sequence or a mutated FRT sequence.

15. A method for preparing a single chain antibody library as described in Paragraph 14 wherein the mutated loxP sequence is lox71, lox66 or lox 5171.

16. A method for preparing a single chain antibody library as described in any one of Paragraphs 1 to 10 wherein the two different non-expression vectors are a vector as depicted in FIG. 6 or 7 and a vector as depicted in FIG. 8 or 9.

17. A method for preparing a single chain antibody library as described in any one of Paragraphs 1 to 16 wherein the host selectively expresses a single chain antibody, which is bound on the surface of phage or released from the surface of phage.

18. A method for preparing a single chain antibody library as described in Paragraph 17 wherein the host selectively expresses a single chain antibody bound on the surface of phage is *E. coli* with a supE mutation, and the host expresses a single chain antibody released from the surface of phage is *E. coli* without a supE mutation.

19. A method for preparing a single chain antibody library as described in any one of Paragraphs 1 to 18 wherein the titer of the VH library is $10^6$ or more.

20. A method for preparing a single chain antibody library as described in any one of Paragraphs 1 to 19 wherein the titer of the VL library is $10^5$ or more.

21. A method for preparing a single chain antibody library as described in any one of Paragraphs 1 to 20 wherein the titer of the single-chain antibody library is $10^{11}$ or more.

22. A method for preparing a single chain antibody library as described in Paragraph 21 wherein the titer of the single chain antibody library is $10^{12}$ or more.

23. A VH library that is obtained by amplifying, by PCR, gene fragments including CDR1 and CDR2 regions of a VH-region and gene fragments including CDR3 of the VH-region in the immunoglobulin gene and shuffling the gene fragments including CDR1 and CDR2 regions of the VH-region and gene fragments including CDR3 of the VH-region, that contains a small amount of contamination of a repertory which cannot be expressed and that is highly stable.

24. A VH library as described in Paragraph 23 obtained by the following steps:
  step (i) for amplifying gene fragments including the CDR1 and CDR2 regions and gene fragments including the CDR3 region in the VH region of the immunoglobulin gene using a human peripheral blood cDNA library and human spleen cDNA library as a template, the primers one of which is selected from Seq. ID Nos. 1-7 and the other of which is Seq. ID No. 8 or 9, and the primers one of which is Seq. ID No. 10 or 11 and the other of which is selected from Seq. ID No. 12-17, respectively; and
  step (ii) for shuffling the gene fragments between gene fragments including CDR1 and CDR2 and gene fragments including CDR3 in the VH region by PCR using two primers, one of which is selected from Seq. ID Nos. 1-7 and the other of which is selected from Seq. ID Nos. 12-17.

25. A VH library as described in Paragraph 23 or 24 whose titer is $10^6$ or more.

26. A VL library that is obtained by amplifying, by PCR, gene fragments including CDR1 and CDR2 regions of the VL-region and gene fragments including CDR3 of the VL-region in the immunoglobulin gene and shuffling the gene fragments including CDR1 and CDR2 regions of the VL-region and gene fragments including CDR3 of the VL-region, that contains a small amount of contamination of a repertory which cannot be expressed and that is highly stable.

27. A VL library as described Paragraph 26 obtained by:
  step (i) for amplifying gene fragments including the CDR1 and CDR2 regions and gene fragments including the CDR3 region of the Vκ region in the immunoglobulin gene by PCR using a human peripheral blood and a spleen cDNA library as a template, and primers, one of which is selected from Seq. ID Nos. 18-21 and the other of which is Seq. ID No. 22 or 23, and primer, one of which is Seq. ID No. 24 or 25, and the other of which is selected from Seq. ID No. 26-29, respectively;
  step (ii) for shuffling the gene fragments between gene fragments including CDR1 and CDR2 and gene fragments including CDR3 in the Vκ region by PCR using two primers, one of which is selected from Seq. ID Nos. 18-21 and the other of which is selected from Seq. ID Nos. 26-29;
  step (iii) for amplifying gene fragments including the CDR1 and CDR2 regions and gene fragments including the CDR3 region of the Vλ region in the immunoglobulin gene using a human peripheral blood cDNA library or spleen cDNA library as a template, and the primers, one of which is selected from Seq. ID Nos. 30-38 and the other of which is selected from Seq. ID No. 39-42, and the primers, one of which is selected from Seq. ID No. 43-46, and the other of which is Seq. ID No. 47 or 48, respectively;
  step (iv) for shuffling the gene fragments between gene fragments including CDR1 and CDR2 and gene fragments including CDR3 in the Vλ region of an antibody by PCR using two primers, one of which is selected from Seq. ID Nos. 30-38 and the other of which is selected from Seq. ID No. 47 or 48; and
  step (v) for mixing the products obtained at step (ii) and gene fragments obtained at step (iv).

28. The titer of a VL library as described in Paragraph 26 or 27 is $10^5$ or more.

29. A single-chain antibody library obtained by using a method as described in any one of Paragraphs 1 to 22.

30. A single-chain antibody library as described in Paragraph 29, the titer of the library is $10^{11}$ or more.

31. A single-chain antibody library as described in Paragraph 30, the titer of the library is $10^{12}$ or more.

32. Non-expression vectors for preparing a single-chain antibody library that is a combination of a promoter-free vector and a SD sequence-free vector.

33. Non-expression vectors for preparing a single-chain antibody library as described in Paragraph 32, the vectors comprising a mutated reverse-oriented repeat sequence obtained by mutating a wild-type reverse-oriented repeat sequence recognized by recombinase.

34. Non-expression vectors for preparing a single-chain antibody library as described in Paragraph 33 wherein the mutated reverse-oriented repeat sequence obtained by mutating a wild-type reverse-oriented repeat sequence recognized by recombinase is a mutated loxP sequence or a mutated FRT sequence.

35. Non-expression vectors for preparing a single-chain antibody library as described in Paragraph 34 wherein the mutated reverse-oriented repeat sequence is lox71, lox66 or lox5171.

36. Non-expression vectors for preparing a single-chain antibody library as described which are obtained by combining a vector illustrated in FIG. 6 or 7 and another vector illustrated in FIG. 8 or 9.

37. An antibody chip using a single-chain antibody library as described in any one of Paragraphs 29 to 31.

38. An antibody chip as described in Paragraph 37 that is a categorized single-chain library.

39. An antibody filter using a single-chain antibody library as described in any one of Paragraphs 29 to 31.

40. An antibody filter as described in Paragraph 39 that is a categorized single-chain library.

41. A method for screening for an antigen-specific antibody using a single-chain antibody library as described in any one of Paragraphs 29 to 31, an antibody chip as described in Paragraphs 37 or 38, or an antibody filter as described in Paragraph 39 or 40.

42. A method as described in Paragraph 41 for screening for an antigen-specific antibody comprising:
    step (a) for bringing an antigen into contact with a single-chain antibody library as described in any one of Paragraphs 29 to 31, an antibody chip as described in Paragraphs 37 or 38, or an antibody filter as described in Paragraph 39 or 40;
    step (b) for detecting a bond between single-chain antibodies and the antigen; and
    step (c) for identifying the single-chain antibodies bound to the antigen.

43. A method as described in Paragraph 41 for screening for an antigen-specific antibody comprising:
    step (a) for bringing an antigen into contact with a single-chain antibody library as described in any one of Paragraphs 29 to 31;
    step (b) for recovering a phage displaying single-chain antibodies bound to the antigen;
    step (c) for neutralizing a solution comprising the phage displaying the single-chain antibodies recovered at step (b);
    step (d) for amplifying the phage obtained at step (c) by means of *E. coli* with a supE mutation;
    step (e) for bringing the antigen into contact with the phage, amplified at step (d), displaying the single-chain antibodies;
    step (f) for detecting a bond between the phage displaying single-chain antibodies and the antigen; and
    step (g) for identifying the single-chain antibodies bound to the antigen.

44. A method for screening for an epitope-specific antibody using a single-chain antibody library as described in any one of Paragraphs 29 to 31, an antibody chip as described in Paragraph 37 or 38, or an antibody filter as described in Paragraph 39 or 40.

45. A method as described in Paragraph 44 for screening for an epitope-specific antibody comprising:
    step (a) for bringing an epitope into contact with a single-chain antibody library as described in any one of Paragraphs 29 to 31, an antibody chip as described in Paragraph 37 or 38, or an antibody filter as described in Paragraph 39 or 40;
    step (b) for detecting bond between single-chain antibodies and the epitope; and
    step (c) for identifying the single-chain antibodies bound to the epitope.

46. A method for screening for an antigen-specific antibody using a single-chain antibody library as described in any one of Paragraphs 29 to 31, an antibody chip as described in Paragraph 37 or 38, or an antibody filter as described in Paragraph 39 or 40.

47. A method as described in Paragraph 46 for screening for an antigen-specific antibody comprising:
    step (a) for bringing an antigen into contact with a single-chain antibody library as described in any one of Paragraphs 29 to 31, an antibody chip as described in Paragraph 37 or 38, or an antibody filter as described in Paragraph 39 or 40;
    step (b) for detecting bond between single-chain antibodies and the antigen; and
    step (c) for identifying the antigen bound to the single-chain antibodies.

48. A method for screening an antigen-specific ligand, using a single-chain antibody library as described in any one of Paragraphs 29 to 31, an antibody chip as described in Paragraph 37 or 38, or an antibody filter as described in Paragraph 39 or 40.

49. A method as described in Paragraph 48 for screening for an antigen-specific ligand comprising:
    step (a) for bringing an antigen into contact with a single-chain antibody library as described in any one of Paragraphs 29 to 31, an antibody chip as described in Paragraph 37 or 38, or an antibody filter as described in Paragraph 39 or 40;
    step (b) for detecting bond between single-chain antibodies and the antigen;
    step (c) for bringing a ligand into contact with the antigen bound to the single-chain antibody library as described in any one of Paragraphs 29 to 31, the antibody chip as described in Paragraph 37 or 38, or the antibody filter as described in Paragraph 39 or 40; and
    step (d) for detecting or step (e) for identifying the ligand bound to the antigen.

50. A method for analyzing/evaluating protein-protein or protein-DNA interaction using a single-chain antibody library as described in any one of Paragraphs 29 to 31, an antibody chip as described in Paragraph 37 or 38, or an antibody filter as described in Paragraph 39 or 40.

51. A method as described in Paragraph 50 for analyzing/evaluating protein-protein or protein-DNA interaction comprising:
    step (a) for bringing an antigen comprising protein or DNA into contact with a single-chain antibody library as described in any one of Paragraphs 29 to 31, an antibody chip as described in Paragraph 37 or 38, or an antibody filter as described in Paragraph 39 or 40;
    step (b) for detecting bond between single-chain antibodies and the antigen;
    step (c) for bringing a different antigen into contact with the antigen bound to the single-chain antibody library as described in any one of Paragraphs 29 to 31, the antibody chip as described in Paragraph 37 or 38, or the antibody filter as described in Paragraph 39 or 40; and
    step (d) for detecting or identifying analogous or different molecules bound to the antigen.

52. A digital screening system for performing, by a digital screening method, a screening method as described in any one of Paragraphs 41 to 49, or the analysis/evaluation of protein-protein or protein-DNA interaction by a method as described in Paragraph 50 or 51.

53. A diagnostic reagent for the diagnosis of various diseases comprising the use of a single-chain antibody library as described in any one of Paragraphs 29 to 31, an antibody chip as described in Paragraph 37 or 38, or an antibody filter as described in Paragraph 39 or 40.

54. A kit for the diagnosis of various diseases comprising a diagnostic reagent for various diseases as described in Paragraph 53.

55. A diagnostic method for the diagnosis of various diseases comprising the use of a diagnostic reagent for various diseases as described in Paragraph 53 or a diagnostic kit for various diseases as described in Paragraph 54.

56. A therapeutic reagent for treating various diseases comprising the use of a single-chain antibody library as described in any one of Paragraphs 29 to 31.

57. A therapeutic method for treating various diseases comprising the use of a therapeutic agent as described in Paragraph 56.

The method for preparing a single chain antibody library according to the present invention comprises shuffling of VH regions in the VH library and VL regions in the VL library by amplifying gene fragments including the CDR1 and CDR2 regions and those including the CDR3 region of the VH or VL region in the immunoglobulin gene by PCR using a cDNA library as a template, inserting the VH library and the VL library obtained from shuffling the gene fragments encoding the CDR1 and CDR2 regions and those encoding the CDR3 region, all of which are in the VH and VL regions, into different non-expression vectors, and introducing these vectors into a host, but the scope of this invention is not limited thereto. The method may comprise shuffling the gene fragments between those for CDR1 region and those for CDR2 and CDR3 regions, and among those for CDR1, CDR2 and CDR3 regions as well as between those for CDR1 and CDR2 regions and those for CDR3 region described above. Alternatively, the method may comprise different shuffling combination between VH region and VL regions, e.g. shuffling in the VH region and non-shuffling in the VL region.

Conventionally, as shuffling method of gene fragments inside the VH region or the VL region, it has been known to mix different DNA molecules cut at random, denature and anneal those DNA molecules and produce thereby heterologous DNA molecules. By this method, however, wrong pairs of DNA strands are easy to be annealed and many mutations occur in the framework portion in the VH and VL regions so that it has been a problem that the efficiency by which functional antibody genes are created.

Furthermore, as shuffling method between VH region and VL region, it has been known to preselect VH or VL region and then select VH or VL region which enhances the affinity of the preselected VH or VL region to the antibody. However, according to this method, selection of region is laboresome. Moreover, when either one is preselected out of the VH and VL regions, its hydrophobic surface of the preselected VH or VL region is exposed and non-specifically bind to some antigen so that, when VH or VL region is selected and forms an antibody molecule, the molecule may not possibly bind to the antigen.

Furthermore, method for shuffling gene fragments between the VH region and the VL region by PCR and by separately subcloning the VH region and the VL region have been known. This method, however, requires two times of cloning and is laboresome to maintain the diversity of single-chain antibodies. Moreover, method for shuffling between the VH region and the VL region by means of DNA recombination using a recombinase has been known (Nature Biotech., 18:75-80, 2000). This method, however, has a problem of instability since the primary library is made by an expression vector of a single-chain antibody. Further, it is difficult to judge whether DNA recombination actually occurs or not, and to selectively prepare single-chain antibodies.

It has never been possible by any methods described above to obtain a single-chain antibody library having a repertory of $10^{11}$ or more.

In contrast, by the methods according to the present invention, it is possible to obtain a single-chain antibody library having a repertory of $10^{11}$ or more, such as $10^{12}$. Furthermore, by the methods according to the present invention, it is possible to obtain a single-chain antibody library more simply and more rapidly and to stably provide such single-chain antibody libraries. Furthermore, by the methods according to the present invention, it is also possible to make screenings for antibodies against plural antigens simultaneously. Moreover, since single-chain antibodies in the present invention can be isolated, for example, as antigen-expressing phage, it is easy to mass-produce the antibodies and to convert them into IgG.

The cDNA library in the present invention is not limited to any specific one, so long as it comprises immunoglobulin (antibody) genes derived from human or other organism, and may include, for example, human or mouse peripheral blood, spleen and bone marrow cDNA libraries.

According to the present invention, shuffling gene fragments between the VH region in a VH-library and the VL region in a VL-library is preferably performed by means of DNA recombination using recombinase.

The method for displaying single-chain antibodies comprising VH and VL regions on the surface of phage particles according to the present invention is preferably a method for displaying only single-chain antibodies on the surface. For example, as illustrated in FIG. 14, the method can be performed by constructing two different non-expression vectors such that a marker gene such as a drug resistance gene is expressed only when a gene fragment for the VH region in the VH library and the VL region in the VL library are shuffled.

The VH library and/or VL library according to the present invention is not limited to any specific one, as long as it comprises the VH region and/or VL region. However, it is preferred that the library contains a small amount of contamination of a repertory that cannot be expressed and is highly stable. The preparation of VH and VL libraries will be detailed below, but the scope of the invention is not limited thereto. It is possible to obtain a VL library whose titer is $10^6$ or more and a VL library whose titer is $10^5$ or more by amplifying gene fragments including the CDR1 and CDR2 regions and the CDR3 region in the VH or VL region of the immunoglobulin gene by PCR using a cDNA library as a template, such as human peripheral blood, spleen and bone marrow cDNA libraries, and primers which can amplify the gene fragments, for example, one or more, preferably all, of the primers having nucleotide sequence of Seq. ID Nos. 1-48, and by shuffling gene fragments between the CDR1 and CDR2 regions and the CDR3 region in the VH and VL regions. Libraries with high quality can be obtained by such methods more simply and more rapidly than by the methods which have been used so far. It is further possible to obtain libraries in which some or all FWs (framework) and CDRs have a mutation derived from mutations by the intrinsic antibody production system, and thus to prepare a repertory which does not exist in vivo. However, since the mutants are derived from the intrinsic antibody production system, it is highly possible that they maintain function and structure as antibody and thus this library has a higher quality than the libraries in which artificial mutations are introduced. However, it is also easy to introduce artificial mutations in a library by modifying PCR condition or using a mutation-inducing reagent.

The two different non-expression vectors in the present invention are not limited to any specific ones, as long as they cannot express the insert alone but combination of two different non-expression vectors enables them to express the VH region and the VL region. Since the present invention utilizes non-expression vectors, VH and VL libraries stably exist and maintenance of the repertory is easy.

The two different non-expression vectors used in the present invention comprise, for example, a pair of promoter-free vector (where no promoter exists) and an SD-sequence free vector (where SD sequence exists), both of which comprise an control sequence that regulates gene expression, such as a mutant reverse-oriented repeat sequence obtained by mutating a wild-type reverse-oriented repeat sequence recognized by recombinase, and a pair of a vector having a sequence of -[promoter]-[lox]-[transcription termination signal]-[lox]-[SD-VH-CH-g3 protein], and a vector having a sequence of (promoterless vector)-([transcription termination signal])-[lox]-[SD-VL-CL]-[lox]-(which is a vector with a transcription termination signal; in which transcription does not proceed to the gene so that translation does not occur, until recombination occurs). Further, the promoter-free vector which comprises a control sequence that regulates gene expression, such as a mutated reverse-oriented repeat sequence obtained by mutating a wild-type reverse-oriented repeat sequence recognized by recombinase, may include expression vectors such as pSABccB-VL2, pSABccB-VL2K, etc. but the scope of the invention is not limited thereto. It should be noted that the linear maps of these vectors are shown in FIGS. 8 and 9, and their preparation is described in Example 2. On the other hand, the SD sequence-free vector which comprise an control sequence that regulates gene expression, such as a mutant reverse-oriented repeat sequence obtained by mutating a wild-type reverse-oriented repeat sequence recognized by recombinase, may include vectors such as pSABccB-VH2, pSABccB-VH3, etc. but the scope of the invention is not limited thereto. It should be noted that the linear maps of these vectors are shown in FIGS. 6 and 7, and their preparation is described in Example 1. Since the above-mentioned pSABccB-VH3 vector incorporates a puromycin-R expression unit, it is possible to select, by using cancer cells as material for screening, antibodies for new drug-discovery and gene therapy, which are taken up by the cells. It was reported that, antibody phages incorporated by such cells release DNA and express the gene if a gene expression unit for animal cells exists on the DNA. (Journal of Molecular Biology, 288:203-211, 1999). Specifically, an antibody library using a pSABccB-VH3 vector is applied to the cells, after two days puromycin is applied to the culture medium, two more days later total DNA is isolated from surviving cells and is introduced into *E. coli*, and ampicillin-resistant colonies can be obtained. Thus, the plasmids derived from the antibody-phage can be recovered. In the actual screening, it is preferable to select the cells with puromycin after the selection of antibody-phage bound to the cells is repeated about three times, thereby amplifying the antibody-phage bound to the cells.

The wild-type reverse-oriented repeat sequence recognized by the above recombinase may include loxP sequence recognized by a recombinase Cre of bacteriophage P, FRt sequence recognized by FLP recombinase derived from yeast *Saccharomyces cerevisiae*, etc. The mutated reverse-oriented repeat sequence obtained by mutating the wild-type reverse-oriented repeat sequence means the sequence of the wild-type reverse-oriented repeat sequence with some mutation, e.g. one or two or more bases of replacement, deletion, and insertion, which changes the substrate specificity in the specific DNA recombination reaction by a recombinase. Such mutant reverse-oriented repeat sequences may include, for example, lox71 comprising a mutated loxP sequence by replacing a part of a reverse-oriented repeat sequence of a wild-type loxP sequence with other bases, lox66 comprising a mutated loxP sequence (Nucleic Acids Research, 25(4):868-872, 1997), lox517, a mutant loxP sequence which is obtained by replacing a part of a spacer region of a wild-type loxP with other bases (Japanese Unexamined Patent Application Publication No. 11-196880), and a mutated FRT sequence which is obtained by replacing a part of the sequence of a wild-type FRT reverse-oriented repeat sequence with other bases. The non-expression vectors described above may include, for example, non-expression vectors derived from chromosomes, episomes or viruses, more specifically, vectors derived from bacterial plasmids, yeast plasmids, vectors derived from papovavirus such as SV40, vaccinia virus, adenovirus, avian sarcoma virus, pseudorabies virus, and retroviruses, bacteriophage, transposon, etc., and their combinations such as cosmids or phagemids which are derived from genetic elements of a plasmid and a bacteriophage.

The host used in the invention is not limited to any specific one, as long as it selectively expresses a single-chain antibody, bound on the surface of organism materials such as phage or released from the surface of organism materials such as phage. To express single-chain antibodies bound on the surface of phages, antibody-displaying phages are produced using *E. coli* with a supF mutation that enable amber translation stop codon just before the sequence encoding phage's surface protein (g3 protein) after lox recombination to translate into an amino acid (FIG. 1). On the other hand, to express single-chain antibodies in a released condition, antibody-displaying phages are infected with *E. coli* without a supF mutation (FIG. 1). Alternatively, plasmids derived from the antibody-displaying phages is are isolated from *E. coli* infected by antibody-displaying phages, the plasmids is are introduced into *E. coli* without supE mutant, and the expression of the antibodies is induced. Suitable hosts may include, for example, prokaryotic cells such as *E. coli, Strectomyces, Bacillus subtilis, Streptococcus, Staphylococcus*, etc., eukaryotic cells such as yeast, *Aspergillus*, etc., insect cells such as *Drosophila* S2, *Spodoptera* Sf9, etc., animal cell lines such as L cell, CHO cell, COS cell, NIH3T3 cell, HeLa cell, C127 cell, BALB/c3T3 cell (containing mutants lacking dihydrofolate reductase, thymidine kinase, etc.), BHK21 cell, HEK 293 cell, Bowes malignant melanoma cell, etc., and plant cell lines. Introduction of a VH vector and/or VL vector into such a host may be performed by any method described in many standard experimental manuals such as those by Davis et al. ("Basic methods in molecular biology, 1986) and Sambrook et al. ("Molecular cloning: a laboratory manual, 2nd Ed., Cold Spring Harbor Laboratory Press, Cold Spring Harbor, N.Y., 1989), for example, competent cells method using chemical reagents such as calcium chloride, calcium phosphate transfection, DEAE-dextran-mediated transfection, transvection, microinjection, cationic lipid-mediated transfection, electroporation, transduction, scrape loading, ballistic introduction, infection by means of phage or virus.

A single-chain antibody library obtained by the method of the present invention and an antibody chip or antibody filter using such a single-chain antibody library do not have problems of contamination of a repertory that cannot be expressed and instability of the library. The library not only allows the screening for an antigen-specific antibody, an epitope-specific antibody, an antibody-specific antigen, a ligand specific to an antigen, and the like but also is useful for the analysis/evaluation of protein-protein interaction or protein-DNA interaction, and diagnosis/therapeutics of various diseases (see FIGS. 1-5, and Example 6).

The antibody chip or filter according to the present invention is not limited to any specific one, as long as the whole or part of a single-chain antibody library is bound. Such an antibody chip or filter may be prepared, for example, by the following method. The antibody-displaying phages to bind to collection of beads each of which has a single peptide attached on its surface (random peptide beads described in "Method: A Companion to Methods in Enzymology," 9:482-493, 1996), or the antibody-displaying phages to bind to a column on which random peptides are attached, or the antibody-displaying phages to bind to biotin-labeled random peptides are recovered using beads that bind to biotin and the like and cloned. The cloned phage is transformed into soluble antibodies by being expressed in *E. coli* without supE mutation and made into a chip (FIG. 1A). Antibody-displaying phages may be made into a chip as they are. To fix antibodies on a chip, various compounds that bind to a 6×His tag located on the C terminal of the antibody portion of soluble antibodies or antibody-displaying phages, for example, NTA provided by Qiagen, or a TALON residue or anti-His tag antibody by CloneTech may be used. The preparation of a chip is described below. A 96-well plate where Ni-NTA provided by Qiagen is attached may be used (FIG. 1B). The peptide sequences bound to those antibodies may be identified by a method based on digital hybridization (W099/31270) (FIG. 2) or a method using the mass spectroscopy (FIG. 3).

A method based on digital hybridization is described below, but the method applicable to the invention is not limited thereto. For example, an antibody chip to which 24 kinds of antibodies are attached is provided (FIG. 2A). One hundred twenty-seven (127) peptide antigens which have different sequences are prepared, labeled with fluorescent dyes, and combined to provide antigen mixtures (MA, M1-M7). MA represents a mixture of all the peptide antigens, while M1-M7 represents digitized peptide mixtures. The digits 0 and 1 of FIG. 2B represent the absence or presence (addition) of each of peptide antigens in the mixture. These antigen mixtures are allowed to separately contact with antibody chips, and spots to which the antigens are bound are identified with fluorescent dyes as an indicator (FIG. 2C). The result is digitized for each spot of antibody chips.

For example, spot 1 (antibody 1) is represented as "11011000" because it bound only to MA, M7, M5 and M4. Since this is a digital indication of antigen peptide 88 (that is, the pattern of mixture into the antigen mixtures), it indicates that the antigen peptide 88 binds to the antigen 1 (FIG. 2D). In the same manner, for all of the antigen peptides, antibodies bound to them can be identified. The amino acid sequences of each of the peptides can be analyzed with a mass spectrum analyzer. By compiling the amino acid sequences of peptides into a database, it is possible to relate the sequence to a peptide with the same sequence by searching for the sequence in the database.

A method using a mass spectrum analyzer (FIG. 3) comprises allowing random peptides to react with an antibody chip, dissociating the peptides bound to each of the spot (antibodies) from the antibodies using urea or the like, and analyzing the amino acid sequence of the peptides with a mass spectrometer (FIG. 3 step (3)). The peptide may include a fragment of a protein, a protein itself, a nucleic acid polymer such as a low molecular weight compound and an RNA aptamer, and the random peptide may include a mixture of the above compounds and a peptide having a limited sequence.

The phages which bind to a collection of beads, each of which a single peptide attached thereto (random peptide beads as described in "Method: A Companion to Methods in Enzymology," 9:482-493, 1996) are selected from a single-chain antibody library (FIG. 4 step (1)), beads to which the phages are bound are isolated (FIG. 4 step (2)), the phage are separately recovered from each of the beads, and then the peptide sequences are determined (FIG. 4 step (3)). In this case, the antibody (phage) may be a mixture comprising plural kinds of antibodies which are capable of binding to the same peptide in contrast with the case depicted in FIG. 3. Alternatively, using *E. coli* display method (Molecular Biology, 301:893-904, 2000) by which the peptides are displayed on the surface of *E. coli*, phages bound to the *E. coli* are selected from the antibody library. At the same time, the *E. coli* that binds to the phages is recovered and the gene fragment encoding the peptide in the vector for the peptide display is sequenced, and the sequence of the peptide is determined. Then, the recovered phage particles are allowed to infect *E. coli* cells for displaying the antibodies, induced to make expression and the soluble single-chain antibodies are recovered. Thus, using a His tag on the C-terminals of the antibodies, glass slides with a metal chelating agent on their surface are prepared and the antibodies can be immobilized on the glass slides.

According to the present invention, methods by which an antibody-antigen binding is detected may be any known method to those skilled in the art. For example, measurement of light absorption, enzyme-linked immunosorbent assay (ELISA), enzyme immunoassay (EIA), radioimmunoassay (RIA), fluorescent immunohistochemistry, or the like may be used, but it is not limited thereto.

The methods for screening for antigen-specific antibodies or epitope-specific antibodies according to the present invention may comprise, for example, a method by which antigens or epitopes attached to beads or a filter are bound to a single-chain antibody library, the antibodies bound thereto are analyzed by mass spectroscopy, the amino acid sequence of the antibodies are determined and search in the database is performed. The method for screening antibody-specific antigens according to the present invention comprises a method by which the whole or a part of a single-chain antibody library of the present invention is attached to beads or a filter and made into contact with the antigens, and then the antibodies bound thereto are analyzed by mass spectroscopy, the amino acid sequences of the antibodies are determined and search in the database is performed.

A method for screening for a ligand specific to an antigen according to the present invention comprises, for example, a method by which a known antigen is attached to beads or a filter and antibodies bound to the antibody are identified from a single-chain antibody library. The method for screening for a ligand (longer peptide or a whole protein) specific to an antigen (peptide) according to the invention also comprises, for example, an antibody are attached to beads or a filter, an antibody chip is prepared, and ligands bound to the antibody are extensively searched from a mixture or an extract. A database which compiles the data obtained as a result of the screening for ligands specific to an antigen as described above may be also included in this invention. It is possible by using such a database to label several kinds of purified proteins or crude extracts of cultured cells and serum with fluorescent dyes, expose them to an antibody chip, wash it, and identify the proteins from the peptide sequences corresponding to spots with the signal (FIG. 5). For example, antibodies specific to the serum proteins are isolated, using beads to which serum proteins are attached, and made into a chip. Serum from patient is applied to an antibody chips and the amount of each of the serum proteins bound to the chip can be measured by applying another specific antibody, labeled with fluorescence or the like, which is different from the antibody on the chip, isolated from the antibody library.

The method for analyzing/evaluating protein-protein interaction or protein-DNA interaction according to the present invention may comprise, for example, a method for analyzing/evaluating the interaction with antigen proteins involved in various diseases such as cancer, allergy, diabetes, hypertension, etc., using single-chain antibodies or genes encoding those antibodies of the present invention. The digital screening system of the present invention means a system for rapidly analyzing/evaluating aforementioned screening methods using a database which has complied data obtained from screenings for antibodies specific to an antigen or epitope, antigens specific to an antibody, ligands specific to an antigen, etc. and analyses/evaluation of protein-protein interaction or protein-DNA interaction.

Single-chain antibody libraries, antibody chips or antibody filters of the present invention can react with antigens in various diseases such as cancer, allergy, diabetes, hypertension, etc., and thus can be used as a effective component in reagents for diagnosis of those diseases. Moreover, they can be applied to a missile therapy or an imaging in a human being with various labels. Furthermore, the single-chain antibody library, antibody chip and antibody filter of the present invention can be used for treatment of various diseases such as cancer, allergy, diabetes, hypertension, etc. Such medicines may be applied orally or parenterally. The oral medicine may comprise solid preparations such as powders, granules, capsules, tablets, etc., or liquid preparations such as syrups, elixirs, etc. The parenteral medicine may comprise injectables, percutaneous agents, or suppositories. These medical preparations can be made by combining an active ingredient with pharmaceutically acceptable supportive additives by conventional methods. Suitable supportive agents may include, for example, when the medicinal preparation is applied orally or via mucosa, an elixir such as softened anhydrous silicate, starch, lactose, crystalline cellulose, etc., a disintegrating agent such as carboxymethyl cellulose, a lustering agent such as magnesium stearate, etc. They may include, when the medicinal preparation is an injectable, a solvent or solubilizer such as physiological saline, mannitol, propylene glycol, etc., an emulsifier such as surfactants, etc. They may include, when they are topically applied, medicinal constituents including a watery or oily solvent or solubilizer, and an adhesive. The dosage of the medicinal preparation may be adjusted according to the disease to be treated, the age, gender, and weight of the patient, the severity of the disease, and the route through which the medicine is applied.

BRIEF DESCRIPTION OF THE DRAWINGS

FIG. 1A illustrates the production of an antigen display phage, the screening method, and the production of soluble antibodies. FIG. 1B illustrates binding of antigen-displaying phage particles to a solid support.

FIG. 2A illustrates a single-chain antibody filter obtained via primary screening. FIG. 2B outlines the preparation of digitally coded antigen mixtures. FIG. 2C illustrates digital screening based on antigen-antibody reaction. FIG. 2D illustrates the relation of antigens with single-chain antibodies by decoding the digitized codes.

FIG. 3(1) illustrates the selection and cloning of peptide-bound phages. FIG. 3(2) illustrates the transformation from phage-displayed antibodies to secreted antibodies by change of hosts for expression. FIG. 3(3) illustrates spots (antibody chip) of antibodies on a plate and analysis by mass spectroscopy and database analysis of the amino acid sequences of the peptides bound to the antibody chip.

FIG. 4(1) illustrates the selection and cloning of phages bound to peptide beads. FIG. 4(2) shows the isolation of the peptide beads. FIG. 4(3) shows the dissociation of antibody-displaying phages and analysis of the amino acid sequences of the peptides bound on the antibody beads (by peptide sequencer or mass spectroscopy) and database analysis.

FIG. 5(1) illustrates the selection of phage particles bound to serum proteins, cloning, and antigen fixation. FIG. 5(2) illustrates transformation of phage-displayed antibodies to secreted antibodies by change of hosts for expression. FIG. 5(3) outlines the serum test.

FIG. 15 presents photos and drawings showing the quality of a novel scFV library.

FIG. 17 shows en example of the amino acid sequences of an scFV. The amino acid sequence of TM1 scFV is represented in the Seq. ID No. 53, the amino acid sequence of O2 (kappa) is in the Seq. ID No. 54, and the amino acid sequence of VH4-34 is in the Seq. ID No. 55.

BEST MODE FOR CARRYING OUT THE INVENTION

The present invention will be specifically described by means of examples, but it should be understood that this invention is not limited thereto in any way.

EXAMPLE 1

Preparation of a VH Vector

Figure 1:
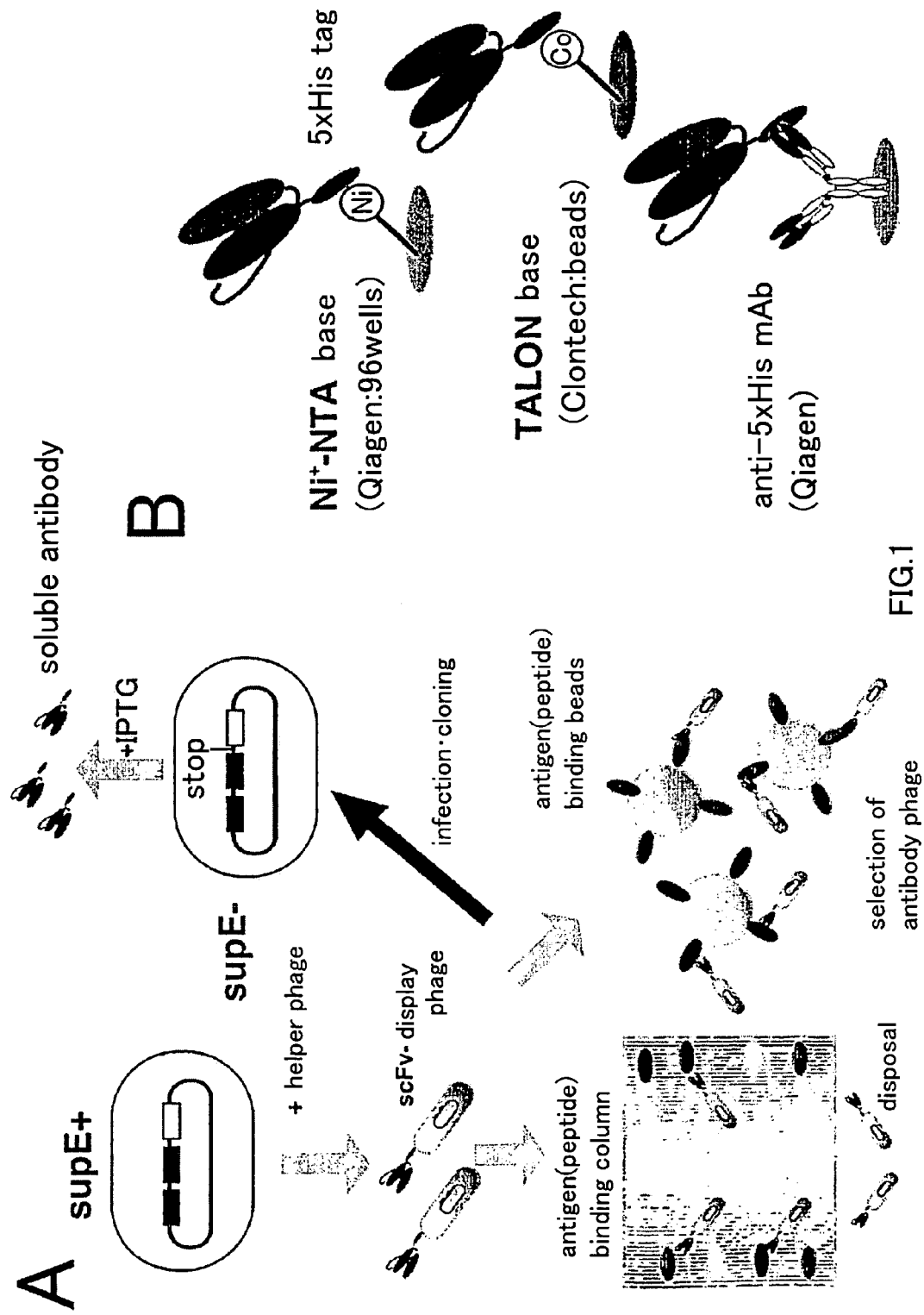
FIG. 1 outlines the process for preparing an antibody chip and antibody filter using a single-chain antibody library of the present invention.
Figure 2:
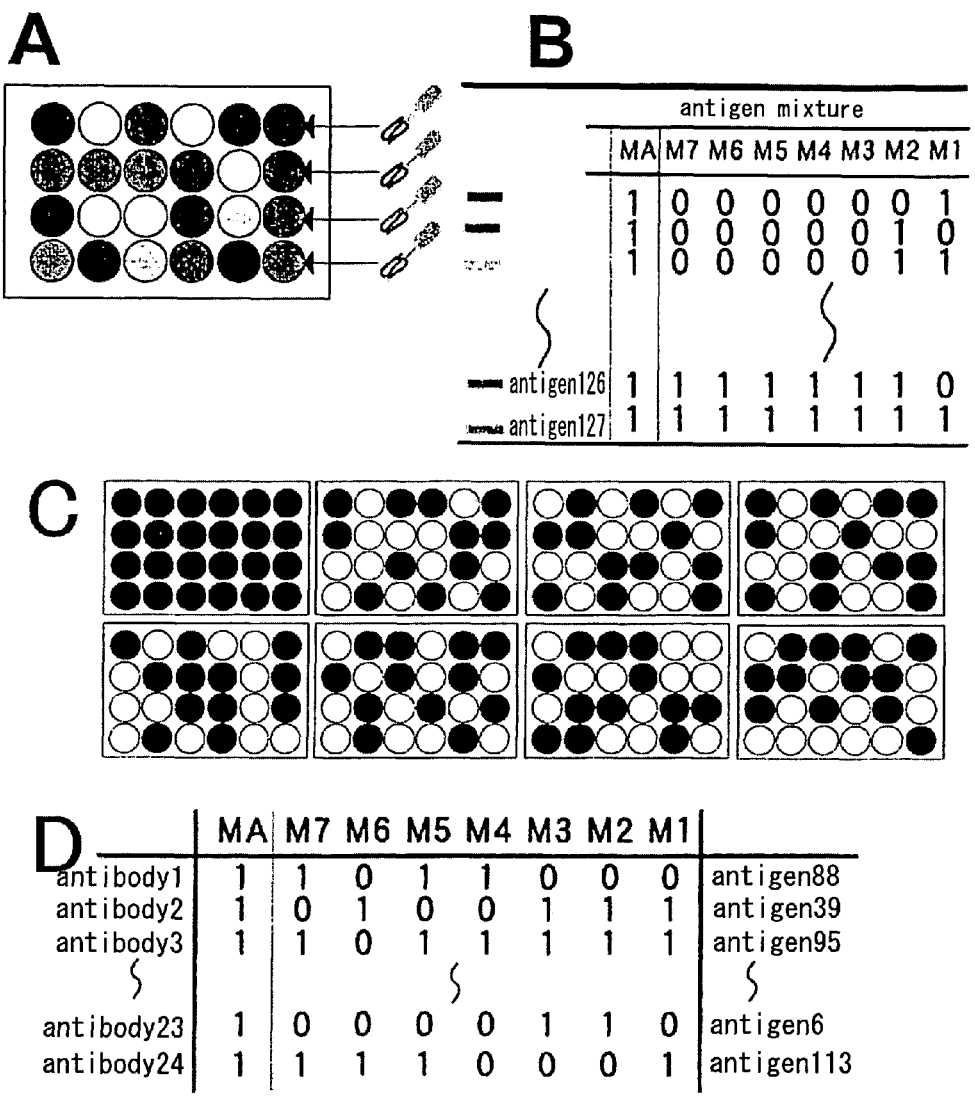
FIG. 2 outlines large-scale transaction for relating antigens to antibodies using a digital screening method.
Figure 3:
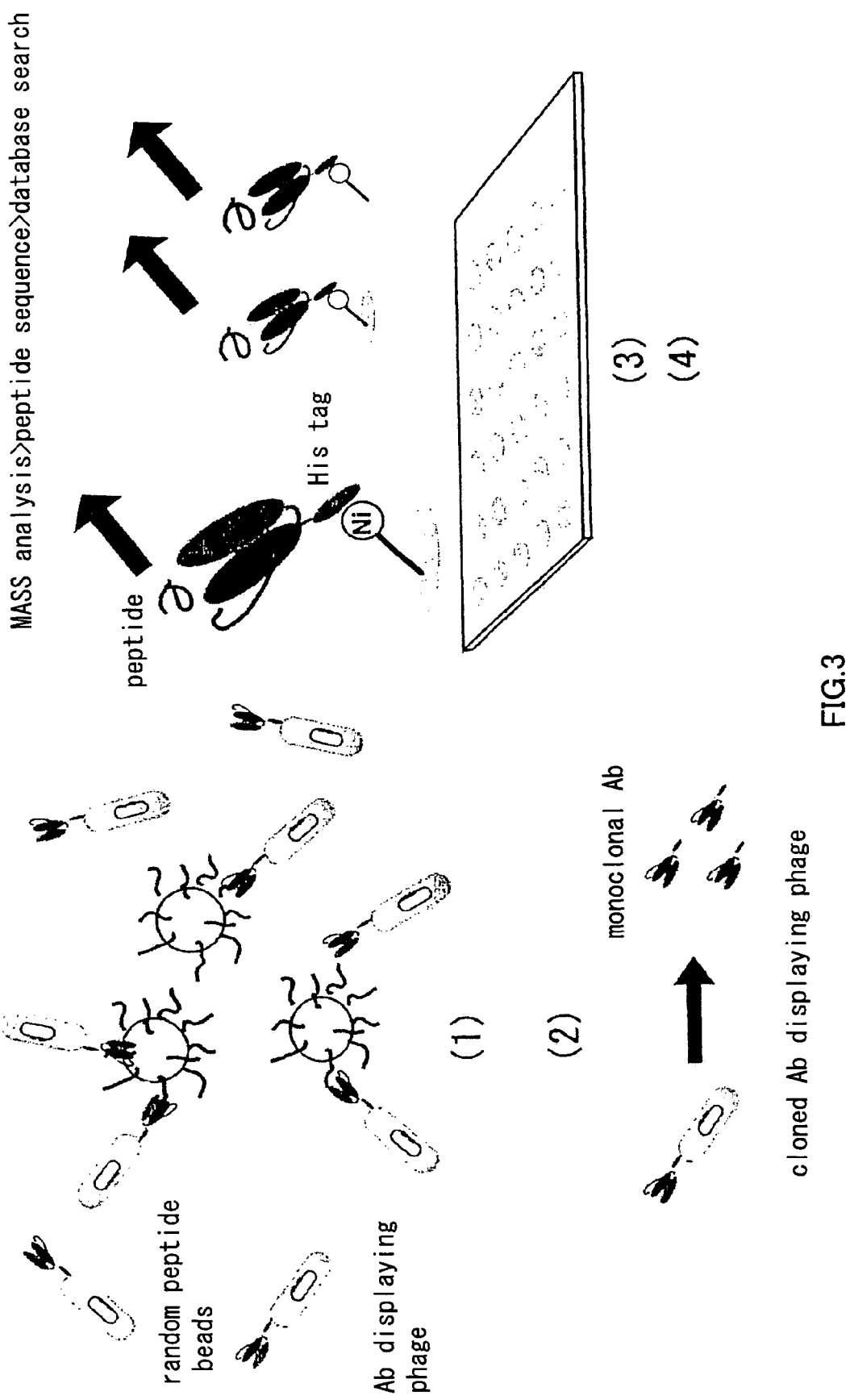
FIG. 3 outlines the search of peptide antibodies and a single-chain antibody library using a mass spectrometer.
Figure 4:
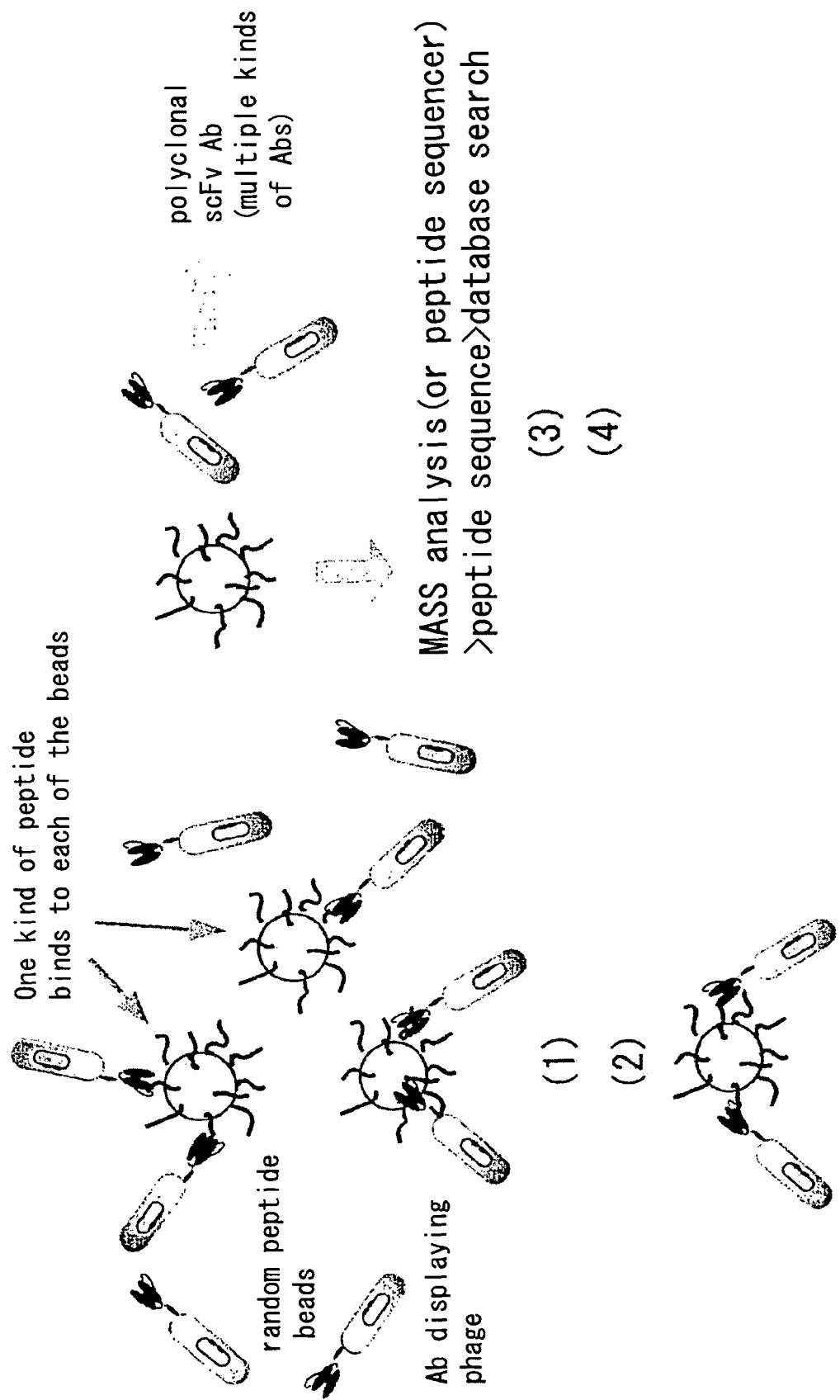
FIG. 4 outlines the search of peptide antigens and a single-chain antibody library using a mass spectrometer.
Figure 5:
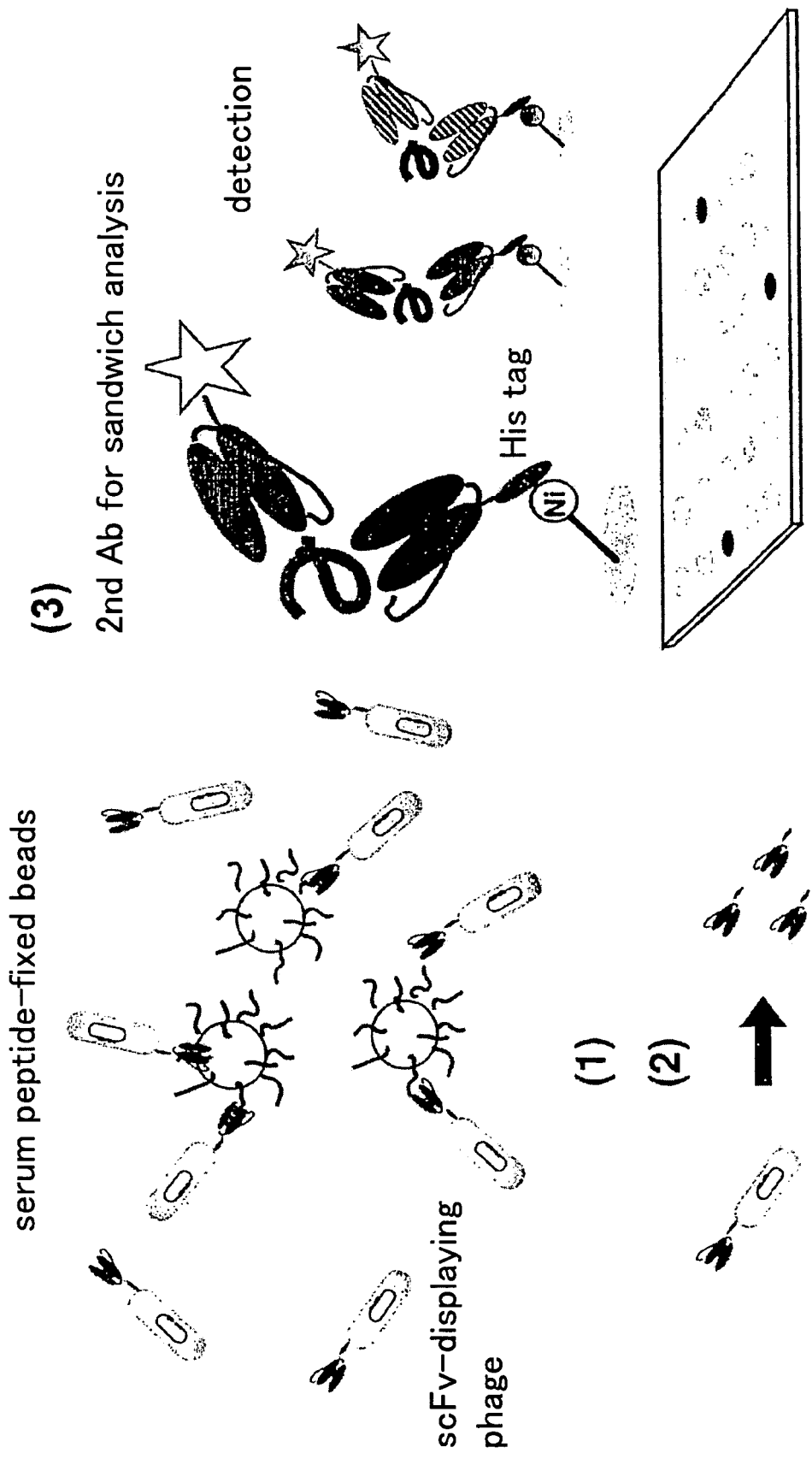
FIG. 5 outlines how to isolate antibodies for serum diagnosis from an antibody library according to the present invention, and a serum test using such an antibody chip.
Figure 6:
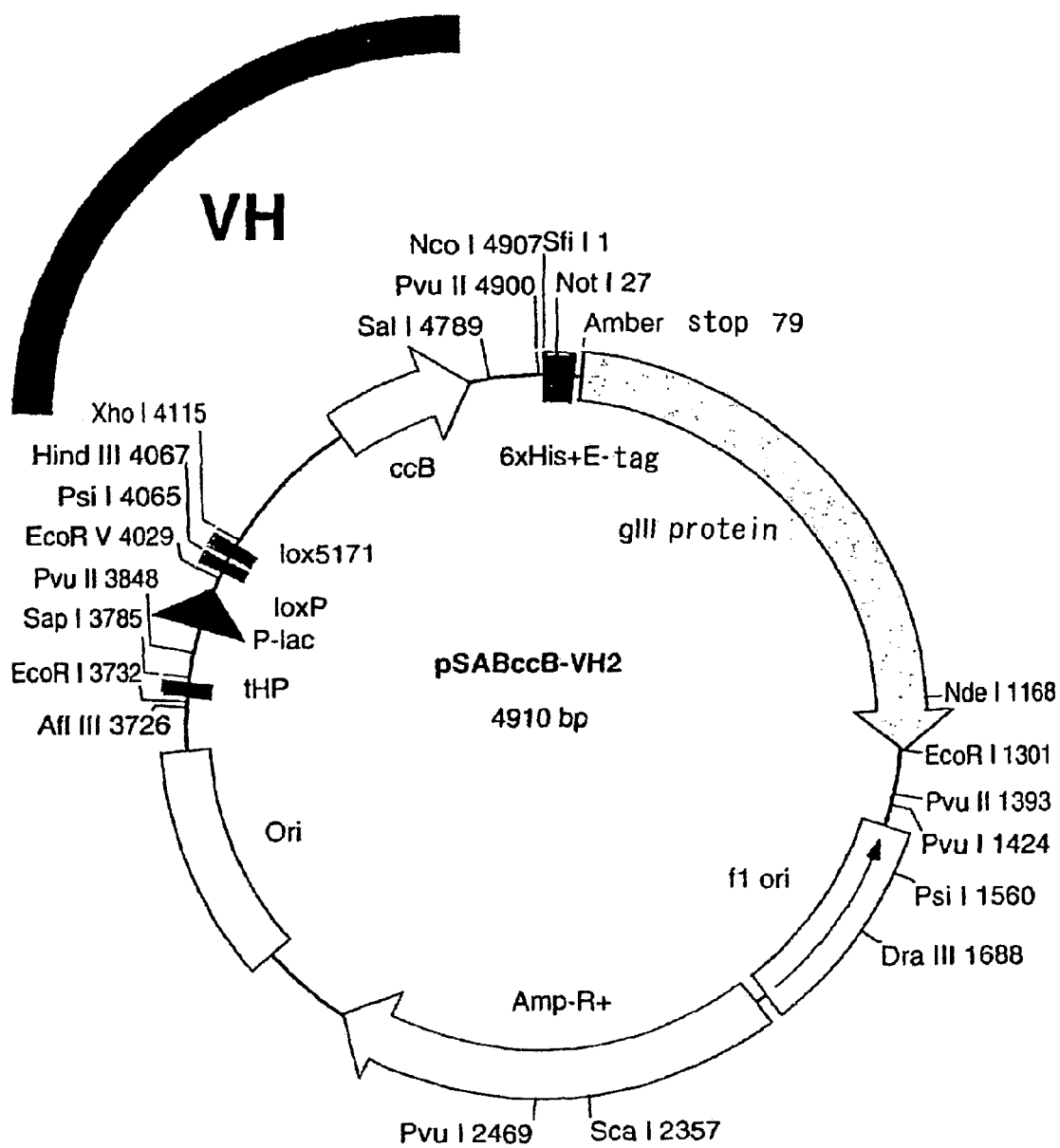
FIG. 6 shows the construction system of a VH vector of the present invention, pSABccB-VH2.
Figure 7:
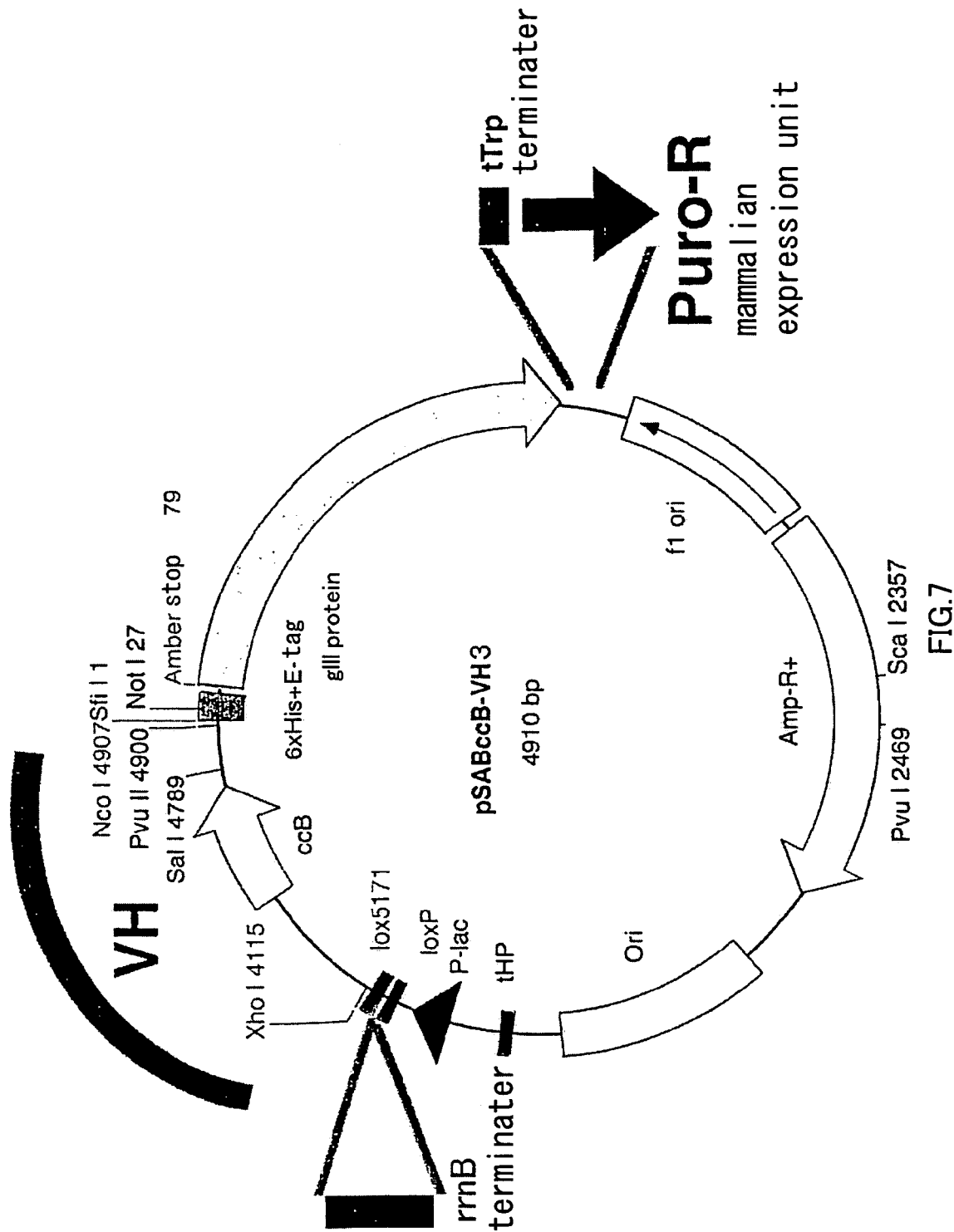
FIG. 7 shows the construction system of another VH vector of the present invention, pSABccB-VH3.

For preparing a VH vector, pBLUESCRIPT II SK(−) (Stratagene) that includes a mutation at an Amp-R portion was used as a basic vector. A fragment containing synthesized tHP (tHP:terminator (Gene, 145:145, 1994)) was inserted into Afl III-Sap I sites, a fragment containing P-lac (lac promoter/operator) of pCANTAB5E (Phainiacia) was inserted into Sap I-EcoR V sites, a fragment containing synthesized loxP and lox5171 was inserted into EcoR V-Xho I sites, an Xho I-Pvu II fragment (fragment containing ccdB) of GATEWAY™ Vector Conversion System (Invitrogen) amplified by PCR was inserted into Xho I-Pvu II sites, and a fragment containing synthesized 6×His, E-tag, Amber STOP 79, and gene for g3 protein was inserted into Pvu II-Pvu II sites, to produce a VH vector pSABccB-VH2 (FIG. 6). To increase expression efficiency, a fragment containing synthesized loxP, rrnB terminator and lox5171 was inserted into EcoR V-Xho I sites, and a fragment containing synthesized 6×His, E-tag, amber STOP codon, gene for g3 protein, tTrp terminator, and Puro-R (puromycin resistant gene) was inserted into Pvu II-Pvu II sites, to produce a VH vector pSABccB-VH3 (FIG. 7).

EXAMPLE 2

Preparation of a VL Vector

Figure 8:
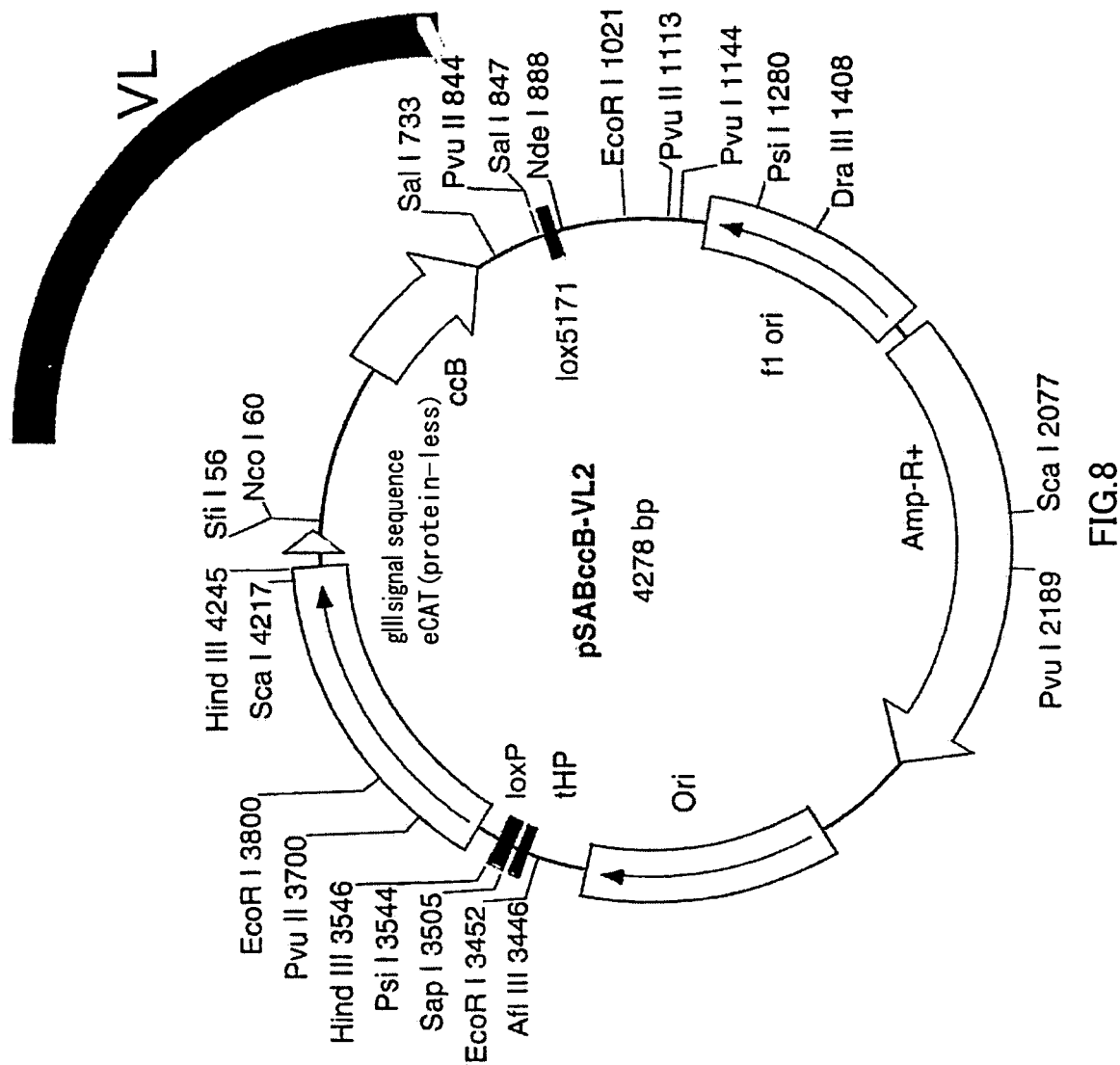
FIG. 8 shows the construction system of a VL vector of the present invention, pSABccB-VL2.
Figure 9:
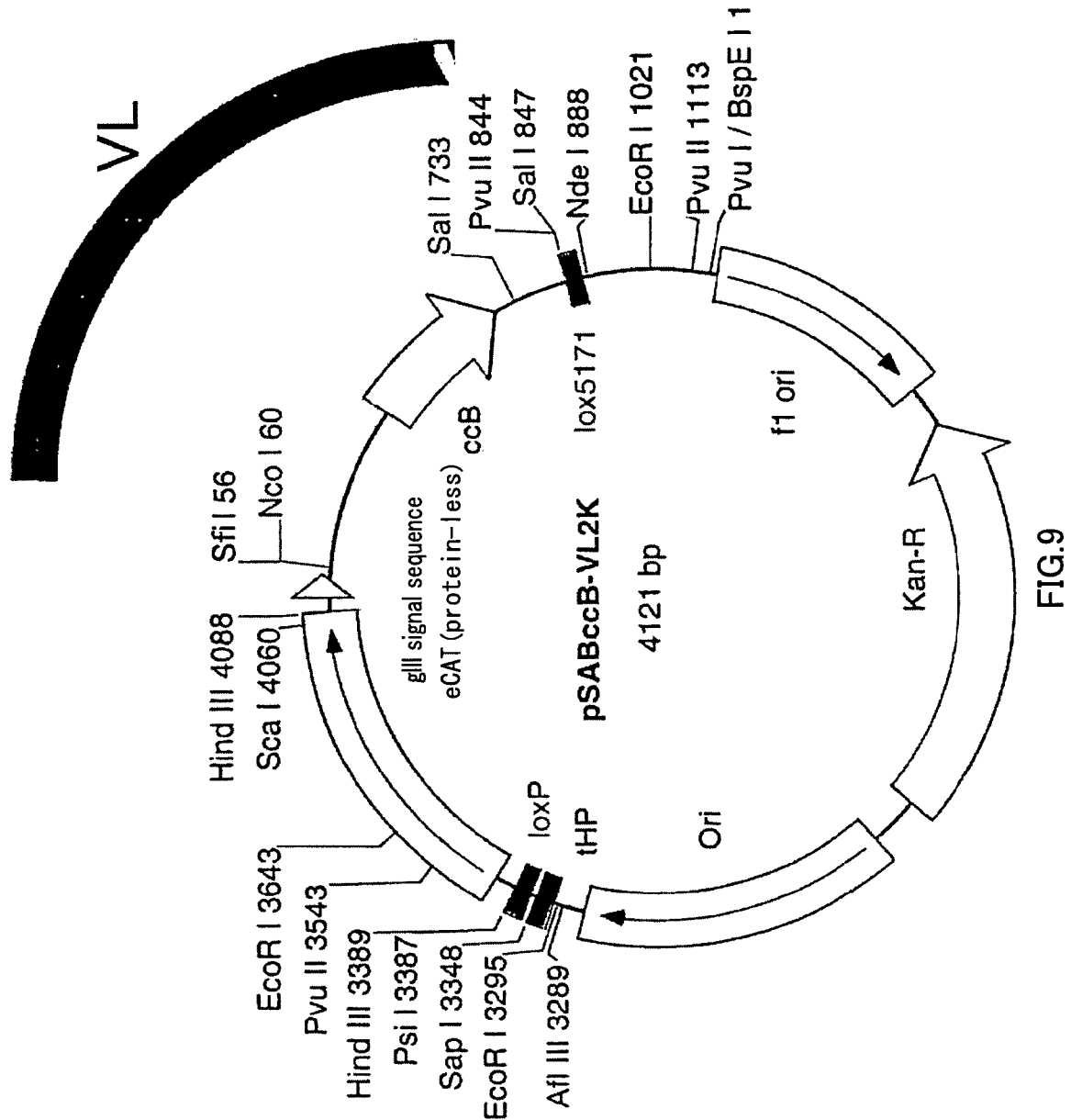
FIG. 9 shows the construction system of another VL vector of the present invention, pSABccB-VL2K.

For preparing a VL vector, pBLUESCRIPT II SK(-) (Stratagene) that includes a mutation at an Amp-R portion was also used as a basic vector. A fragment containing synthesized tHP and loxP was inserted into Afl III-Hind III sites, a fragment (containing eCAT (promoter-less)) containing a Chloramphenicol resistant gene (with a modified SD sequence) derived from BAC (containing a SIM2 gene) amplified by PCR was inserted into Hind III-Hind III sites, a Hind III-Sfi I fragment (containing a g3 signal sequence) of pCANTAB5E (Pharmacia) was inserted into Hind III-Sfi I sites, an Sfi I-Sal I fragment (containing ccdB) of GATEWAY™ Vector Conversion System amplified by PCR was inserted into Sfi I-Sal I sites, a fragment containing synthesized lox5171 was inserted into Sal I-Nde I sites, and an Nde I-Pvu I fragment of pCANTAB5E (Pharmacia) was inserted into Nde I-Pvu I sites, to produce a VL vector pSABccB-VL2 (FIG. 8). To check whether E. coli is transformed with both VH and VL vectors, a VL vector pSABccB-VL2K (FIG. 9) was prepared by replacing Pvu I/BspE I-Afl III fragment of the aforementioned VL vector pSABccB-VL2 with a BspE I-Afl III fragment containing Kan-R of pET24b (Novagen).

EXAMPLE 3

Preparation of VH Library

Figure 10:
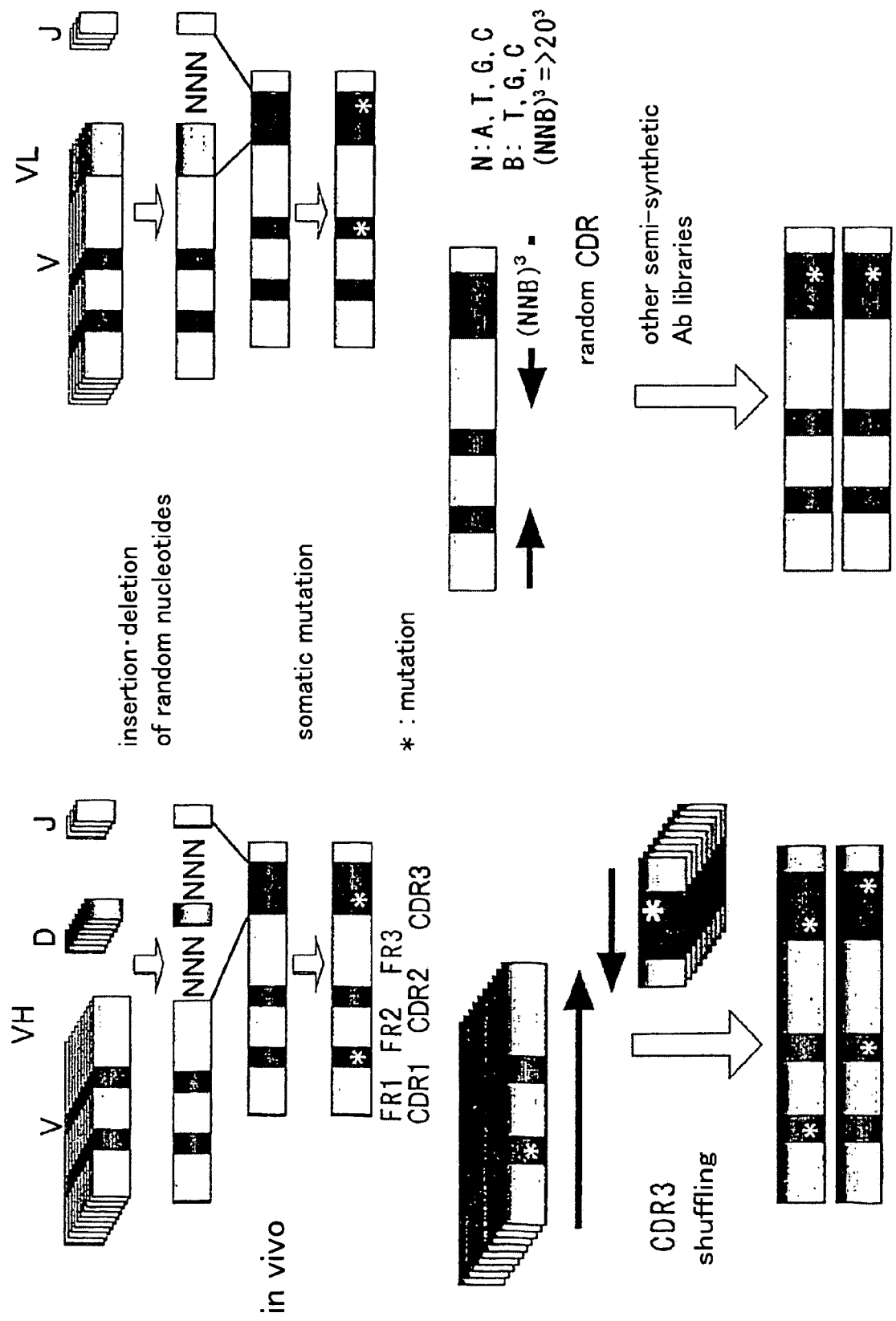
FIG. 10 outlines the CDR3 shuffling.
Figure 11:
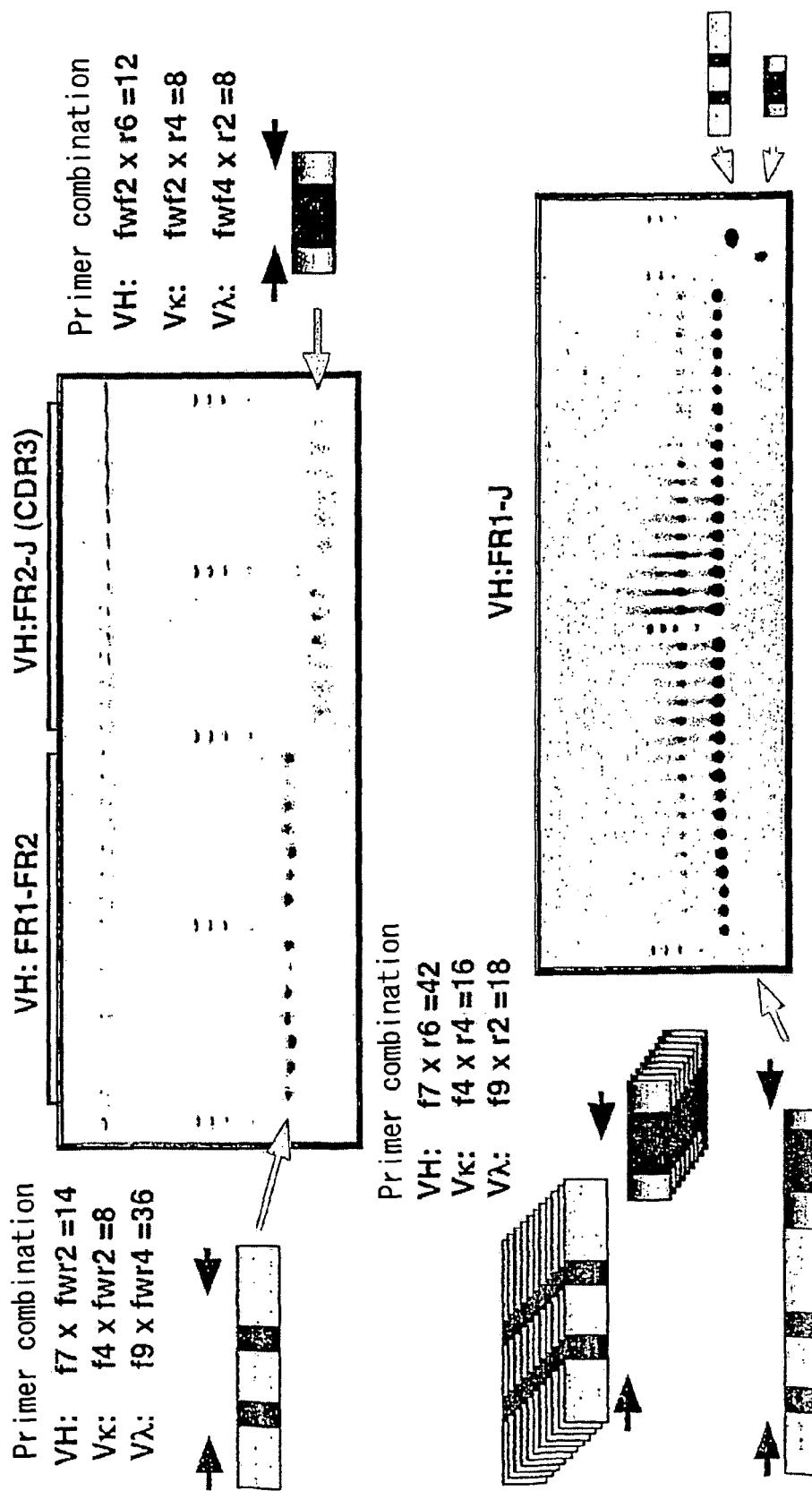
FIG. 11 presents photos and drawings illustrating the VH:CDR3 shuffling.
Figure 12:
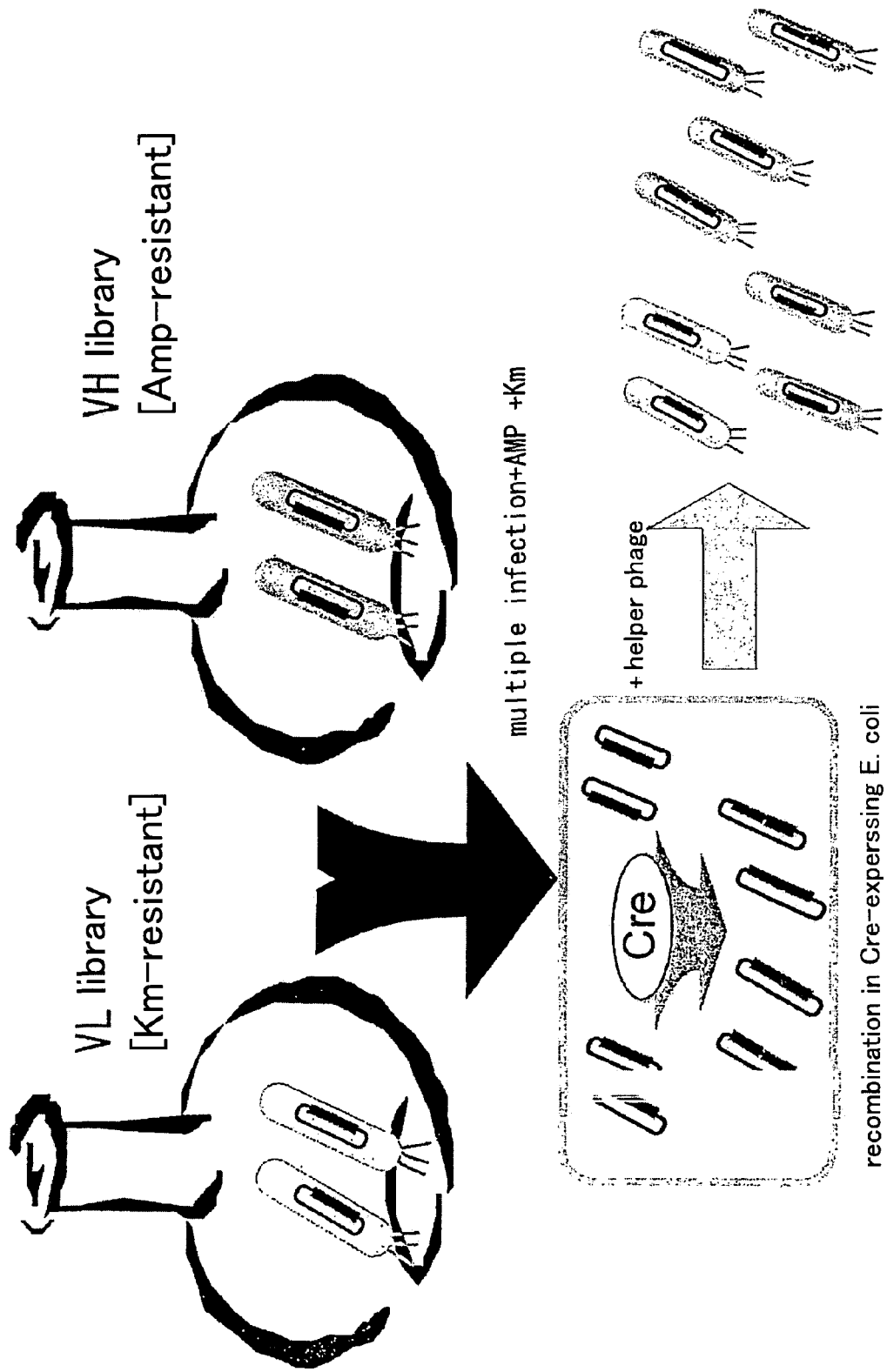
FIG. 12 illustrates how a novel scFV library is prepared.
Figure 13:
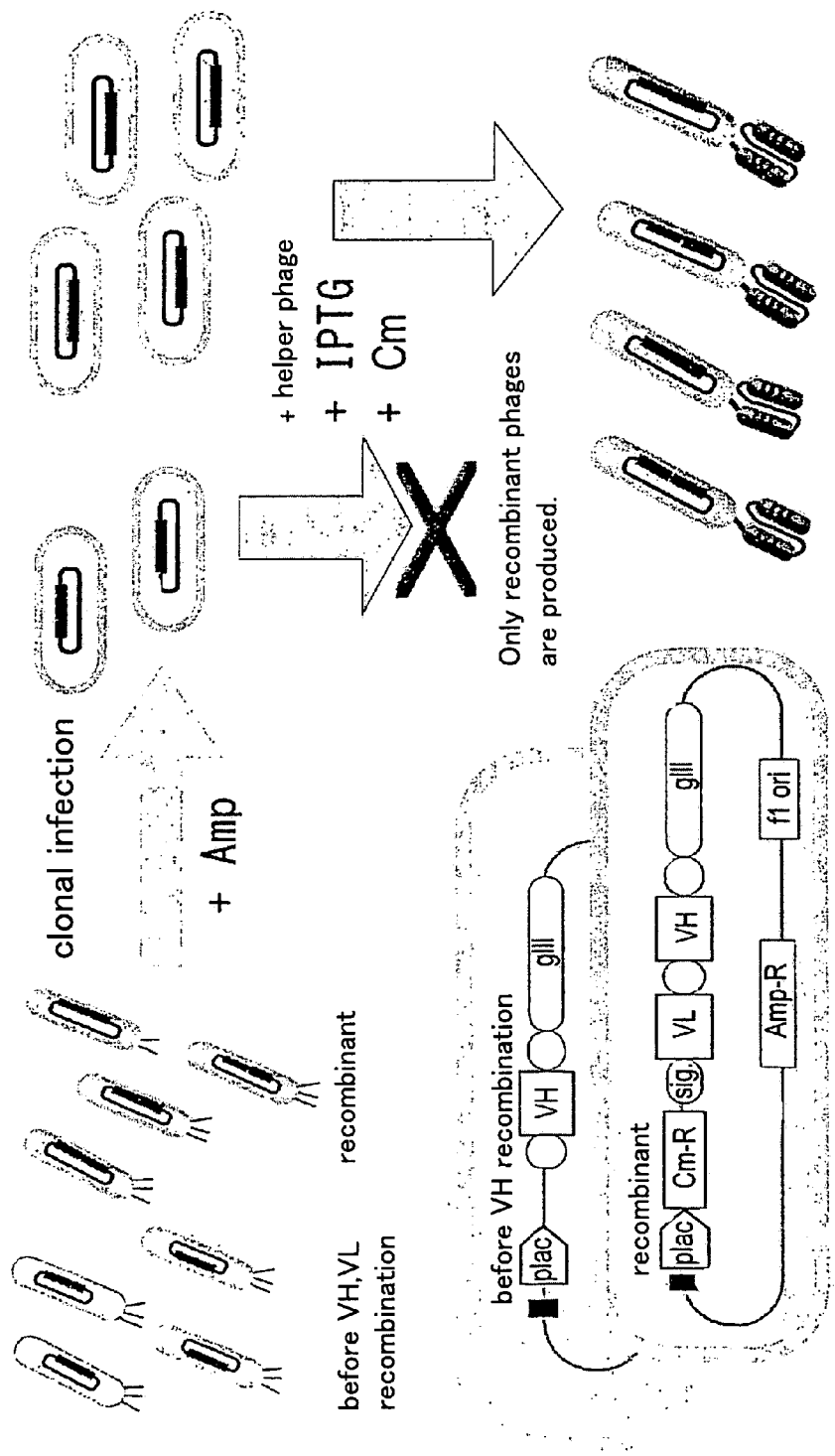
FIG. 13 illustrates how a novel scFV library is prepared, which is a continuation of FIG. 12.

The VH and VL regions in an immunoglobulin (antibody) gene assembly were separately amplified using human peripheral blood cDNAs as a template. To produce a repertory not observed in an organism, shuffling of the antigen recognition region (hyper-variable region or CDR3) was performed (FIG. 10). The VH gene fragment was amplified by PCR using a combination of primers shown below using cDNAs from human peripheral blood or spleen as a template. PCR amplification of the gene fragment (about 250 bp) including the CDR1 and CDR2 regions and the gene fragment (100 bp) including the CDR3 region was performed using <VH-Foward1> shown in Seq. ID Nos. 1-7 and <VH-Reverse2> shown in Seq. ID No. 8 or 9 and using <VH-Forward2> shown in Seq. No. 10 or 11 and <VH-Reverse1> shown in Seq. Nos. 12-17, respectively, so that 14 gene fragments of about 250 bp and 12 gene fragments of 100 bp were obtained (FIG. 11). PCR was performed by the following condition: 94° C. for 2 minutes and 30 cycles of 94° C. for 30 sec, 60° C. for 30 sec, and 72° C. for 30 sec. Individual gene fragments obtained by PCR were subjected to agarose-gel electrophoresis, and gel portions containing the gene fragments were cut out and the gene fragments were purified. The purified gene fragments were mixed with primers of <VH-Reverse1> or <VH-Forward2>, and the resulting mixtures were named VH(FWR3)For1, VH(FWR3)For2, VH(FWR3)Back1, and VH(FWR3)Back2 pools. The VH(FWR)For1 and VH(FWR3)Back1 were combined and the VH(FWR3)For2 and VH(FWR3)Back2 pools were combined, to provide VH1 and VH2 pools, respectively. The VH1 or VH2 pool was amplified by PCR under different combinations of <VH-Forward1> and <VH-Reverse1> (7×6=42 combinations), to produce gene fragments encoding a total length of a VH region. Thus, 84 different gene fragments (42×2) thus obtained were subjected to agarose-gel electrophoresis (FIG. 11), were separated from the gel, and purified. PCR was performed by exposing the sample to 94° C. for 2 minute and seven cycles of 94° C. for 1 minute and 63° C. for 4 in the absence of primers, then, after adding the primers, to 94° C. for 1 minute, 10 cycles of 55° C. for 30 sec, and 72° C. for 1 min, 10 cycles of 94° C. for 15 sec, 60° C. for 30 sec, and 72° C. for 45 sec and finally 72° C. for 45 sec for extension. The purified gene fragments encoding the total length of a VH region were combined, double-digested by restriction enzymes Xho I and Nco I and inserted into the Xho I-Nco I-digested VH vector pSABccB-VH2 or pSABccB-VH3 prepared in Example 1 and ligated thereto. E. coli (XL1-Blue or XL2-Blue) was transformed with the VH vector and was cultivated on agar plates that contained 1% glucose and 50 μg/ml ampicillin and a VH library (whose titer is $10^6$ or more) was obtained. The library were recovered using 10% glycerol, and frozen-stored at −80° C.

EXAMPLE 4

Preparation of VL Library

In the same manner as in Example 3, the Vκ gene fragments were prepared. PCR amplification of gene fragments (about 250 bp) including the CDR1 and CDR2 regions and gene fragments (100 bp) including the CDR3 region in the Vκ region was performed using <Vkappa-Foward1> shown in Seq. ID Nos. 18-21 and <Vkappa-Reverse2> shown in Seq. ID No. 22 or 23 and using <Vkappa-Forward2> shown in Seq. No. 24 or 25 and <Vkappa-Reverse1> shown in Seq. Nos. 26-29, respectively. As a consequence, 8 gene fragments of about 250 bp and 8 gene fragments of 100 bp were obtained. PCR was performed by exposing a gene fragment sample to 94° C. for 2 minutes and 30 cycles of 94° C. for 30 sec, 60° C. for 30 sec, and 72° C. for 30 sec. Individual gene fragments obtained by PCR were subjected to agarose-gel electrophoresis, gel portions containing gene fragments were cut out, and the gene fragments were purified. The purified gene fragments were mixed with the primers <Vkappa-Reverse1> and <Vkappa-Forward2>, and the resulting mixtures were named VK(FWR3)For1, VK(FWR3)For2, VK(FWR3)Back1, and VK(FWR3)Back2 pools. The VK(FWR3)For1 and VK(FWR3)Back1 pools were combined and the VK(FWR3)For2 and VK(FWR3)Back2 pools were combined, to provide Vκ1 and Vκ2 pools, respectively. The VK1 or VK2 pool was amplified by PCR under different combinations of <Vkappa-Forward1> and <Vkappa-Reverse1> (4×4=16 combinations), to produce gene fragments encoding a total length of a VH region. Thus, 32 different gene fragments (16×2) obtained were subjected to agarose-gel electrophoresis, were separated, and purified. PCR was performed by exposing the fragment to 94° C. for 2 minute, seven cycles of 94° C. for 1 minute, and 63° C. for 4 minutes in the absence of primers, and then, adding the primers, to 94° C. for 1 minute, 10 cycles of 55° C. for 30 sec, and 72° C. for 1 minute, 10 cycles of 94° C. for 15 sec, 60° C. for 30 sec, and 72° C. for 45 sec and finally 72° C. for 7 minute for extension.

In the same manner as in Example 3, the Vλ gene fragments were isolated. PCR amplification of gene fragments (about 250 bp) including the CDR1 and CDR2 regions in a Vλ region was performed using <Vlambda-Foward1> shown in Seq. ID Nos. 30-38 and <Vlambda-Reverse2> shown in Seq. ID Nos. 39-42. Gene fragments (100 bp) including the CDR3 region in the Vλ region were amplified by PCR using <Vlambda-Forward2> shown in Seq. Nos. 43-46 and <Vlambda-Reverse1> shown in Seq. No. 47 or 48. As a consequence, 36 gene fragments of about 250 bp and 8 gene fragments of 100 bp were obtained. PCR was performed by exposing a gene fragment sample to 94° C. for 2 minutes and 30 cycles of 94° C. for 30 sec, 60° C. for 30 sec, and 72° C. for 30 sec. Individual gene fragments obtained by PCR were subjected to agarose-gel electrophoresis, and gel portions containing the gene fragments were cut out, and the gene fragments were purified. The purified gene fragments were mixed with the primers <Vlambda-Reverse1> and <Vlambda-Forward2>, and the resulting mixtures were named VL(FWR3)For1, VL(FWR3)For2, VL(FWR3)Back1, and VL(FWR3)Back2 pools. The VL(FWR3)For1 and VL(FWR3)Back1 pools were combined and the VL(FWR3)For2 and VL(FWR3)Back2 pools were combined, to provide Vλ1 and Vλ2 pools, respectively. The Vλ1 or Vλ2 pool was amplified by PCR under different combinations of <Vlambda-Forward1> and <Vlambda-Reverse1> (9×2=18 combinations), to produce gene fragments encoding a total length of a VH region. Thus, 72 different gene fragments (18×4) thus obtained were subjected to agarose-gel electrophoresis, and were separated, and were purified. PCR was performed by exposing a gene fragment sample to 94° C. for 2 minute, seven cycles of 94° C. for 1 minute, and 63° C. for 4 minutes in the absence of primers, and then, adding the primers, 10 cycles of 94° C. for 1 minute, 55° C. for 30 sec, 10 cycles of 72° C. for 1 minute, and to 94° C. for 15 sec, 60° C. for 30 sec, and 72° C. for 45 sec and finally 72° C. for 7 minute for extension.

Both the purified gene fragments encoding the total length of Vκ and Vλ regions were combined, digested by two restriction enzymes Nco I and Sal I, and inserted into the Nco I-Sal I digested VL vector pSABccB-VL2 or pSABccB-VL2K prepared in Example 2 and ligated thereto. $E.\ coli$ (XL1-Blue or XL2-Blue) was transformed with the VL vector and cultivated on an agar plate that contained 1% glucose and 50 μg/ml ampicillin or 50 μg/ml kanamycin. A VL library (whose titer is $10^5$ or more) was obtained. The library was recovered by means of 10% glycerol, and frozen-stored at –80° C.

EXAMPLE 5

Preparation of an Antibody Library by Recombination Between VH and VL Vectors

Figure 14:
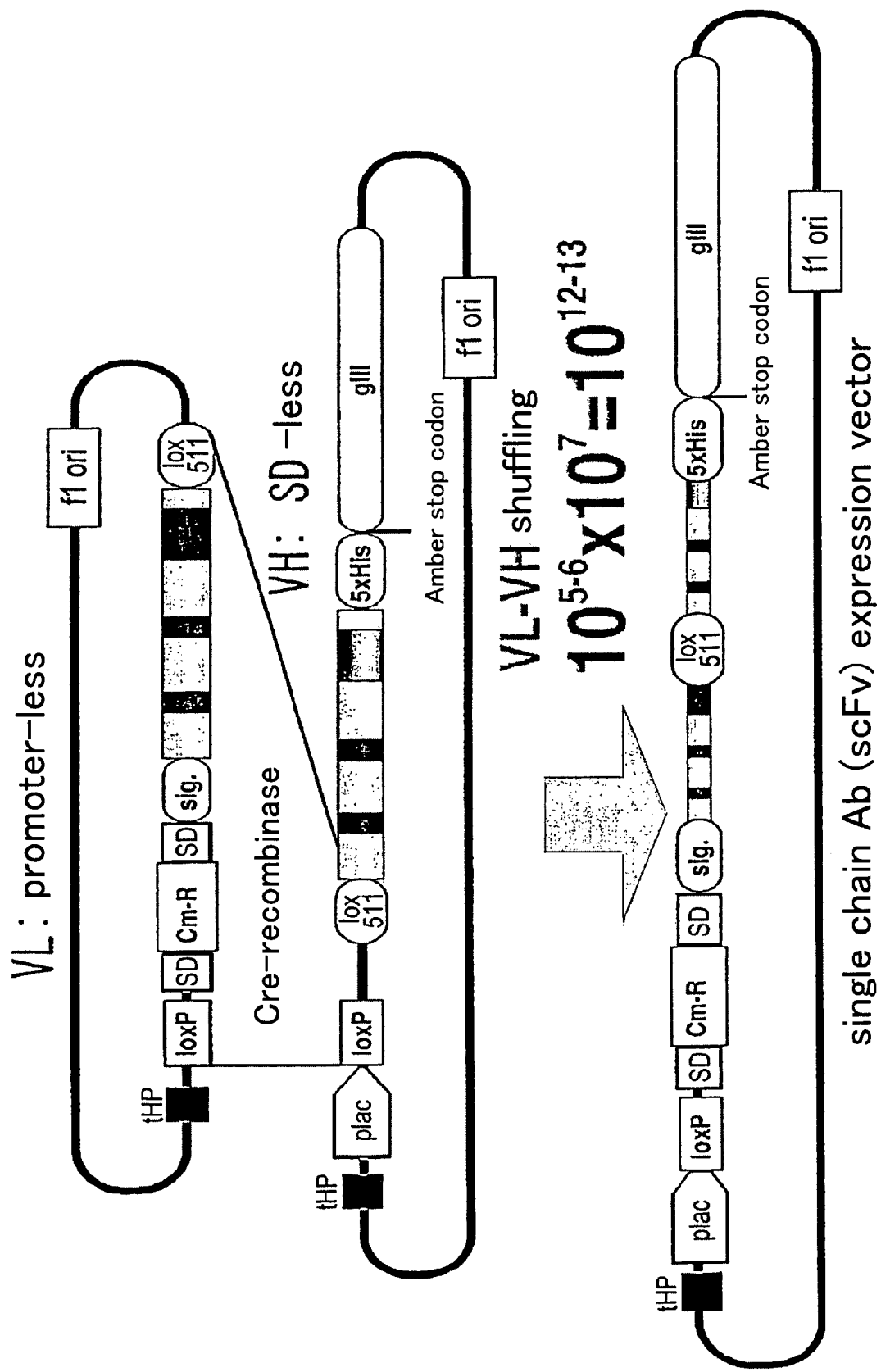
FIG. 14 illustrates the construction of an expression vector for a single-chain library of the present invention.

The VH $E.\ coli$ was inoculated into a 25 ml medium containing 50 ug/ml ampicillin, was infected by a helper phage VCSM13 (Stratagen) under a multiplicity of infection (MOI) of 10, was incubated overnight to isolate the phage. A supernatant of the culture medium was recovered to measure the MOI. In the same manner, VL $E.\ coli$ derived from pSABccB-VL2K prepared in Example 4 was inoculated into a 25 ml of culture medium containing 50 ug/ml kanamycin to isolate the phage. $E.\ coli$ cells for recombination (Cre10F, self-made) were co-infected with the VH and VL phages in a 25 ml of culture medium under the MOI=10. One hour later, 50 .mu.g/ml ampicillin and 50 ug/ml kanamycin were added and the culture was incubated overnight so as to allow the recombination between the VH and VL vectors by a recombinase (FIG. 14). The entire culture medium was transferred to 1 L of a newly-prepared medium containing 50 ug/ml ampicillin and $E.\ coli$ was infected with a helper phage VCSM13 under MOI=10, and the culture was incubated overnight to isolate the phage in the supernatant, whose titer was measured. Then, with the recombinant phage, $E.\ coli$ cells (XL1Blue) was infected in 8 L of a culture medium under MOI=0.5, was incubated at 37° C. for 1 hour, to which 50 ug/ml ampicillin and 1 mM IPTG for inducing the expression of antibody-phage fused proteins as well as a helper phage VCSM13 (MOI=10) were added, and was further incubated at 37° C. One hour later, 50 ug/ml kanamycin for selecting VCSM-infected bacteria (phage-producing bacteria) and 12.5 ug/ml chloramphenicol for double-selecting antibody-expressing bacteria were added to the medium. The temperature of the medium was lowered to 30° C. and was incubated overnight. The supernatant was recovered, and a ⅙ volume of the solution containing 2.5 M NaCl and 30% PEG6000 was added thereto. The antibody-displaying phage particles were precipitated and recovered by centrifugation. The precipitated phage particles were suspended in SM medium, DMSO was added to 7%, and was frozen-stored at –80° C. The antibody phage library was diluted with LB medium, $E.\ coli$ TG1 strain was infected, and incubated on agar plates containing 50 ug/ml ampicillin and 1% glucose to form colonies at 30° C. overnight. The titer (cfu: colony forming units) of the antibody displaying phage was determined by counting the number of colonies and 180 ml of $1.2 \text{.times.} 10^{13}$ cfu/ml, i.e. totally $2 \times 10^{16}$ cfu, was obtained. Minimal amounts of the bacterial cells for each clones were suspended in a PCR solution (20 ul), subjected to PCR amplification using a primer 5'-CGTGAAAAAATTATTATTCGCAATTCC-3' (Seq. ID No. 49) and a primer 5'-ACGCGGTTCCAGCG-GATCCGGATA-3' (Seq. ID No. 50) under the condition of 94° C. for 1 minute, and 30 cycles of 94° C. for 20 sec, 50° C. for 10 sec, and 68° C. for 40 sec, and the immunoglobulin gene region was amplified. The amplified gene fragments were applied to 1% agarose gel electrophoresis, and their lengths were determined (FIG. 15). Out of 32 clones, 28 clones had a normal immunoglobulin gene. The PCR products were sequenced using the primer, and the corresponding genome sequence was searched by IgBLAST to turn out to be derived from various genomic immunoglobulin genes (Table in FIG. 15).

Since a library made by combination of a $10^6$ kinds of VH and a $10^5$ kinds of VL were prevented from decrease of number of the kinds by increasing the amount of the culture at each stage, it contains $10^6 \times 10^5$, i.e. $10^{11}$ kinds. Thus, the total number of recombinant phages contained in 1 ml is $2 \times 10^{13} \times 0.8$=about $2 \times 10^{12}$. Namely, 1 ml contains about 20 cfu of phage that display the same antibody.

EXAMPLE 6

Screening for Specific Antibodies from an Antibody Library

Figure 16:
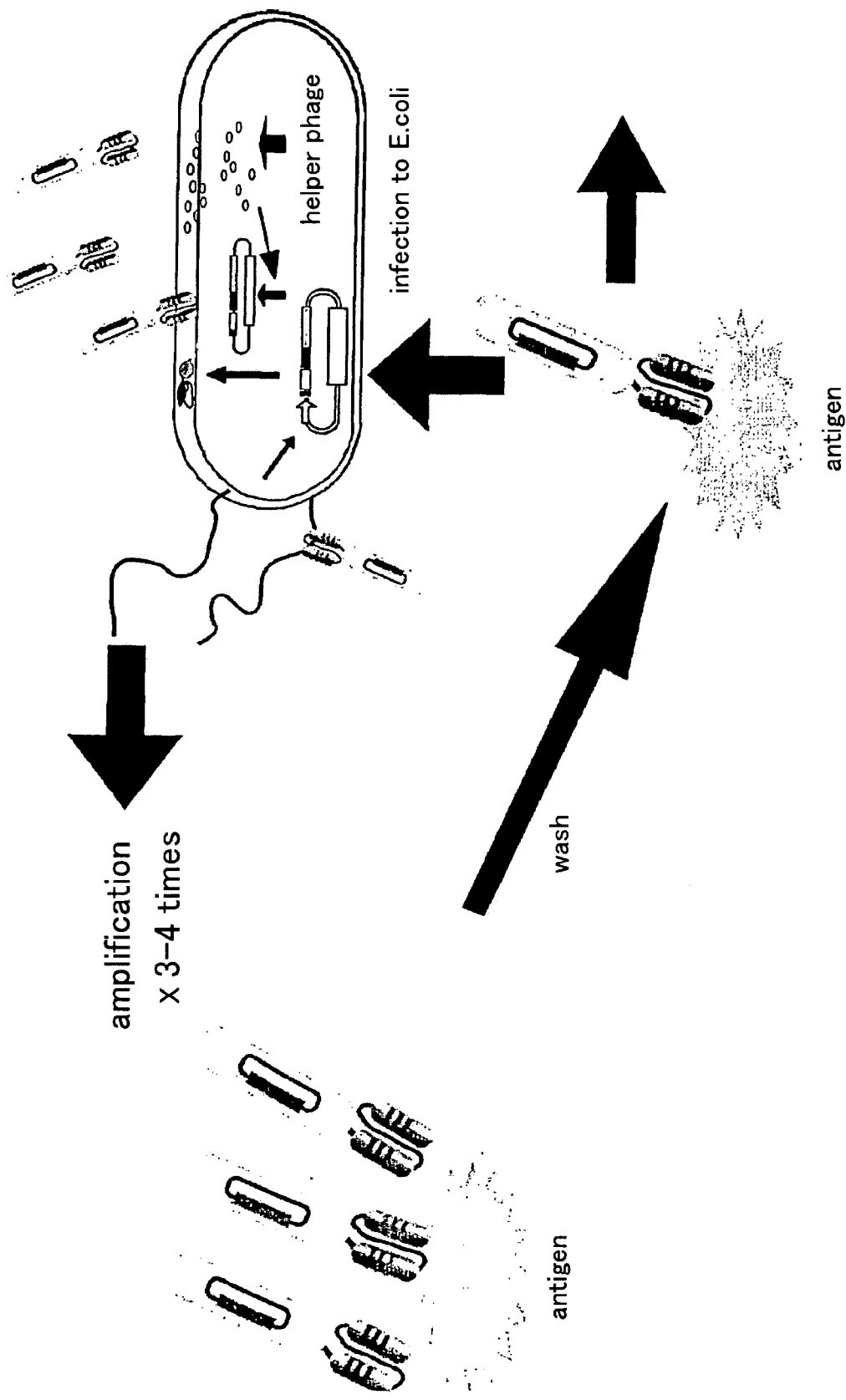
FIG. 16 outlines the method for screening.

Using an FITC-labeled BSA (A-9771, Sigma), a peptide (TM1 or N'-TRVTSFLDWIHEQMERDLKT-C' (Seq. ID No. 51), a peptide (TM2 or N'-PAPSHLVEKIVYHSKYKPKR-C' (Seq. ID No. 52), and recombinant Parking protein expressed and purified in *E. coli* as antigens, an antibody library was screened for specific antibodies (FIG. 16).

A 50 μg of the antigen was dissolved in 1.3 ml of carbonate buffer (0.1M NaHCO3, pH 8.6), and distributed to 48 wells of a 96-well plate in 25 μl aliquots. The plate was covered with a plate seal and the antigen solution was allowed to expand over the entire bottom surface and was left at 4° C. overnight. The plate seal was removed, the antigen solution was discarded, 150 μl of BB (25 mM MOPS, 150 mM NaCl, 3% BSA (232100, Sigma)) was added to each well, and the plate was left at 37° C. for 1 hour. To 1 ml of an scFv library, 2 ml of MBST (25 mM MOPS, pH 7.0, 0.150 mM NaCl, 0.5% Tween20), 2 ml of BB, and 250 μl of 10% Tween20 were added and mixed. The mixture was left at 37° C. for 1 hour. The BB was discarded from each well, which was rinsed with MBST two times, 50 μl of a diluted solution of the scFv library was transferred to each well, a plate seal was applied over the plate, and the plate was gently stirred at 37° C. for 1 hour. The diluted solution of the scFv library was discarded from each well, which was rinsed with MBST ten times. To recover the phage bound to the antigen, 100 μl of TAE (100 mM Triethylamin, pH 11) was applied to each well and the plate was left at room temperature for 10 minutes. Then, 50 μl of TAE was applied to each well, and the plate was left at room temperature for 20 minutes. The recovered phage solution was added to 100 μl of NR (0.66 M MOPS, pH 7.0, 0.1% BSA) to be neutralized. *E. coli* (TG1) which had been cultivated at 37° C. in SBSM (10 mM MOPS, pH 7.0, 20 mM MgCl2, 3% tryptone, 2% yeast extract, 1% NaCl) to give an OD600 of 0.6, were added to the phage solution and was incubated at 37° C. for 30 minutes to allow the recovered phage to infect the *E. coli*. The *E. coli* was spread on LBG-C agar plates (1% tryptone, 0.5% yeast extract, 1% NaCl, 1% glucose, 2% BACTO Agar, 50 μg/ml Carbenicillin) and incubated at 30° C. overnight to allow colony foimation.

The colonies were suspended in 25 ml of SBS (10 mM MOPS, 0.3% tryptone, 2% yeast extract, 1% NaCl) to be recovered. A 0.5 ml of the recovered *E. coli* solution was suspended in 40 ml of SBS, Carbenicillin (50 μg/ml) and a VCSM13 helper phage ($10^{11}$ pfu), and IPTG (1 mM) were added the culture was incubated with gently stirring at 37° C. for 1 hour, Kanamycin (50 μg/ml) and Chloramphenicol (12.5 μg/ml) were added, and the culture was further incubated at 37° C. for 15 hours with stirring. The culture medium was centrifuged at 15000×g at 4° C. for 15 minutes to allow bacterial cells to precipitate and the supernatant containing antibody-displaying phages was recovered. ¼ volume of PEG-NaCl (20% PEG8000, 2.5 M NaCl) solution was added and mixed, and the mixture was kept in ice for 15-30 minutes and centrifuged at 15000×g at 4° C. for 15 minutes to precipitate phage particles. The phage precipitate was suspended in 800 μl of MBS (25 mM MOPS, pH 7.0, 150 mM NaCl) supplemented with 1 μl of Benzonase (Merck), to which 200 μl of BB and 50 μl of 10% Tween20 were added, and the phage suspension was left at 37° C. for 1 hour. On the other hand, 50 μg of the antigen was dissolved in 1.0 ml of carbonate buffer and the resulting antigen solution was transferred to an immunotube, which was left at 4° C. overnight with stirring. The antigen solution was discarded and 3.3 ml of BB was added to the tube, which was left at 37° C. for 1 hour. The BB was discarded and the phage solution (3 ml) was transferred, which was stirred at 37° C. for 1 hour. The phage solution was discarded from the tube, which was then washed 5 times with MBST, 5 times with MBSS (25 mM MOPS, pH 7.0, 500 mM NaCl), and 2 times with MBS. The tube was rinsed once with 3 ml of GH (100 mM Glycine-HCl, pH 2.7), and filled further with GH to the brim, and was left at room temperature for 10 minutes. The tube was rinsed 2 times with MBS to be neutralized, rinsed once with TEA, filled with TEA to the brim, and was left at room temperature for 10 minutes. The TEA was discarded, 500 μl of TEA was newly added, and the tube was sealed with a parafilm. The tube was stirred at room temperature for 20 minutes so that the solution spread all over the space within the tube. 300 μl of NR was added and mixed to neutralize the solution. 2 ml of *E. coli* (TG1) which had been cultivated at 37° C. in SBSM to give an OD600 of 0.6, was added, the tube was sealed with a parafilm and mixed, and left at 37° C. for 1 hour to allow the phage to infect the bacteria. The entire solution was transferred to 40 ml of SBS, to which a VCSM13 helper phage ($10^{11}$ pfu), Carbenicillin (50 μg/ml), and IPTG (1 mM) were added, and the culture was incubated at 37° C. for 1 hour. Later, Kanamycin (25 μg/ml) and Chloramphenicol (25 μg/ml) were added to the culture, which was further incubated for 15 hours. The culture medium was centrifuged at 15000×g at 4° C. for 15 minutes, to precipitate bacterial cells. Then, the supernatant containing antigen-displaying phage was recovered. ¼ volume PEG-NaCl (20% PEG8000, 2.5 M NaCl) solution was added and mixed, and the mixture was kept in ice for 15-30 minutes and centrifuged at 15000×g at 4° C. for 15 minutes to precipitate phage particles. The phage precipitate was suspended in 800 μl of MBS (25 mM MOPS, pH 7.0, 150 mM NaCl) supplemented with 1 μl of Benzonase (Merck), to which 200 μl of BB and 50 μl of 10% Tween20 were added, which was left at 37° C. for 1 hour. On the other hand, 50 μg of the antigen was dissolved in 1.0 ml of carbonate buffer, and the antigen solution was transferred to an immunotube, which was left at 4° C. overnight with stirring. The antigen solution was discarded and 3.3 ml of BB was added to the tube, which was left at 37° C. for 1 hour. The BB in the tube was discarded and the phage solution (3 ml) was transferred, which was stirred at 37° C. for 1 hour. The phage solution was discarded from the tube, which was then washed 5 times with MBST, 5 times with MBSS (25 mM MOPS, pH 7.0, 500 mM NaCl), and 2 times with MBS. The tube was rinsed once with 3 ml of GH (100 mM Glycine-HCl, pH 2.7), and filled further with GH to the brim, and was left at room temperature for 10 minutes. The tube was rinsed 2 times with MBS to be neutralized, rinsed once with TEA, filled with TEA to the brim, and was left at room temperature for 10 minutes. The TAE was discarded, 500 μl of TAE was newly added, and the tube was sealed with a parafilm. The tube was stirred at room temperature for 20 minutes so that the solution spread all over the space within the tube. 300 μl of NR was added to neutralize the solution. 2 ml of *E. coli* (TG1), which had been cultivated at 37° C. in SBSM to give an OD600 of 0.6, was added to the tube, which was then sealed with a parafilm. The tube was agitated, and left at 37° C. for 1 hour to allow the phage to infect the *E. coli* cells. The entire solution was transferred to 40 ml of SBS, to which a VCSM13 helper phage ($10^{11}$ pfu), Carbenicillin (50 μg/ml), and IPTG (1 mM) were added, and the culture was incubated at 37° C. for 1 hour. Later, Kanamycin (25 μg/ml) and Chloramphenicol (12.5 μg/ml) were added to the culture, which was further incubated for 15 hours. The culture solution was centrifuged at 15000×g at 4° C. for 15 minutes, to precipitate bacterial cells to precipitate. Then, the supernatant containing antigen-displaying phage particles was collected. ¼ volume of PEG-NaCl (20% PEG8000, 2.5 M NaCl) solution was added and mixed, and the mixture was kept in ice for 15-30 minutes, and centrifuged at 15000×g at 4° C. for 15 minutes, to precipitate phage. The phage precipitate was suspended in 800 μl of MBS (25 mM MOPS, pH 7.0, 150 mM NaCl) supplemented with 1 μl of Benzonase (Merck), to which 200 μl of BB and 50 μl of 10% Tween20 were added, and the phage suspension was left at 37° C. for 1 hour. On the other hand, a 50 μg sample of the antigen was dissolved in 1.0 ml of carbonate buffer and the resulting antigen solution was transferred to an immunotube, which was left at 4° C. overnight with stirring. The antigen solution was discarded and 3.3 ml of BB was added to the tube, which was left at 37° C. for 1 hour. The BB was discarded, and the phage solution (3 ml) was transferred and was stirred at 37° C. for 1 hour. The phage solution was discarded from the tube, which was then washed 5 times with MBST, 5 times with MBSS (25 mM MOPS, pH 7.0, 500 mM NaCl), and 2 times with MBS. The tube was rinsed once with 3 ml of GH (100 mM Glycine-HCl, pH 2.7), and filled further with GH to the brim, and was left at room temperature for 10 minutes. The tube was rinsed 2 times with MBS to be neutralized, rinsed once with TEA, filled with TEA to the brim, and was left at room temperature for 10 minutes. The TEA was discarded, 500 µl of TEA was newly added, and the tube was sealed with a parafilm. The tube was stirred at room temperature for 20 minutes so that the solution spread all over the space within the tube. 300 µl of NR was added to neutralize the solution. 2 ml of E. coli (TG1) which had been cultivated at 37° C. in SBSM to give an OD600 of 0.6, was added, the tube was sealed with a parafilm, the solution was mixed and left at 37° C. for 1 hour to allow the phage to infect E. coli. The E. coli solution was diluted with SBS, and spread over an LBG-C agar plate and the culture was incubated at 37° C. to form colonies. Bacteria from each colonies were inoculated in 50 µl of SBSGC (10 mM MOPS, pH 7.0, 0.3% tryptone, 2% yeast extract, 1% NaCl, 1% glucose, 50 µg/ml Carbenicillin) in wells of a 96 well-plate using a tooth pick. The plate was covered with a plate seal, and incubated at 37° C. overnight. A VSCM13 phage ($10^{11}$ cfu), IPTG (1 mM), and Carbenacillin (50 µg/ml) 50 µl each were added to each well, to be mixed with the above culture medium (10 µl). The culture was incubated at 37° C. for 1 hour with stirring. 50 µl of SBS containing IPTG (1 mM), Carbenicillin (50 µg/ml), Kanamycin (20 µg/ml), and Chloramphenicol (12.5 µm/ml) was added to each well and the culture was incubated at 37° C. for 15 hours with stirring. The plate was centrifuged at 3000 rpm for 10 minutes to precipitate bacterial cells. The supernatant was mixed with 50 µl of BB and was left at 37° C. for 1 hour (phage solution). ELISA plated were prepared as follows: 50 µg of the antigen was dissolved in 2.6 ml of carbonate buffer and 25 µl of the solution was distributed to each well of the plate, was left at 4° C. overnight, and the antigen solution was discarded. A 150 µl of BB was distributed to each well of the ELISA plate, and was left at 37° C. for 1 hour. The BB was discarded from the ELISA plate, and the total vol of phage solution was distributed to each plate, and was left at 37° C. for 1 hour. Each well was washed 10 times with MBST, 50 µl of an HRP-labeled anti M13 antibody diluted 1000-fold with MBST+BB (1/10 volume) was added to each well, and the plate was left at 37° C. for 1 hour. Each well was washed 10 times with MBST, 100 µl of a coloring solution was distributed to each well, and was incubated at room temperature for 20 minutes. Then, 50 µl of a stopper solution (2M H2SO4) was applied to each well, and the light absorption at 492 nm was measured for each well using a plate reader (model 550, Biorad) (Table 1)

TABLE 1

|  | (1)/(2) > (3) |
|---|---|
| FITC (-BSA) | 54/72 |
| TM1 | 36/72 > 4 |
| TM2 | 58/72 |
| Engineered protein | 26/64 > 6 |

(1) The number of ELISA positive clones. (2) The number of studied clones. (3) The number of independent clones having different nucleotide sequences From the colonies which were positive in the light absorption measurement, DNA of immunoglobulin gene was amplified by PCR. PCR was performed according to the description of an instruction manual, using a primer 5'-CGT-GAAAAAATTATTATTCGCAATTCC-3' (Seq. ID No. 49) and a primer 5'-ACGCGGTTCCAGCGGATCCGGATA-3' (Seq. ID No. 50) at 1 uM and KOD-plus (Toyobo), under the following condition: 94° C. for 2 minute, and then 30 cycles of 94° C. for 30 sec, 50° C. for 10 sec, and 68° C. for 40 sec. The amplified DNA fragments were purified with a Qiaquick PCR purification kit (Qiagen), made a reaction using the primers used in PCR and a BigDye Terminator Cycle Sequencing Kit (Applied Biosystems), purified by gel filtration and was sequenced with a 3730×1 DNA analyzer (Applied Biosystems). The immunoglobulin-encoding portions out of the determined nucleotide sequences were translated into amino acid sequences and then compared with the amino acid sequences of antibodies encoded by the genomic genes using IG-BLAST.

INDUSTRIAL APPLICABILITY

According to the present invention, it is possible to provide a single-chain antibody library free from problems such as the contamination of a repertory that cannot be expressed or instability, and an antibody chip and antibody filter using the library. The single-chain antibody library, and an antibody chip and antibody filter using the library are useful for screening for antigen-specific antibodies, epitope-specific antibodies, antibody-specific antigens, or ligands bound to a antigen, for analyzing/evaluating protein-protein interaction or DNA/protein interaction, and for diagnosing/treating various diseases.

The invention claimed is:

1. A method for preparing a single chain antibody library having a repertory of at least $10^{11}$ comprising:
    step (a) amplifying nucleic acid sequences comprising the CDR1 and CDR2 regions and the CDR3 region of the VH and VL region in an immunoglobulin gene by PCR using a cDNA library as a template to generate gene fragments;
    step (b) shuffling said gene fragments between a first gene fragment and a second gene fragment, wherein the first gene fragment comprises the CDR1 and CDR2 regions and the second gene fragment comprises the CDR3 region in each of the VH and VL regions to produce a VH library and a VL library;
    step (c) inserting said VH library into a first non-expression vector comprising an f1 ori and a first drug-resistance gene, and said VL library into a second non-expression vector comprising an f1 ori and a second drug-resistance gene, wherein one of said first and second non-expression vectors is a promoter-free vector comprising a third drug-resistance gene with a Shine-Dalgarno (SD) sequence and the other non-expression vector is a Shine-Dalgarno (SD) sequence-free vector and wherein the third drug resistance gene is different from the first and second drug resistance genes;
    step (d) shuffling gene fragments between the VH region in the VH library and the VL region in the VL library by introducing both the VH library-incorporated non-expression vector and VL library-incorporated non-expression vector into a host;
    step (dd) recombining the two non-expression vectors to create recombined expression vectors comprising an antibody gene whereby co-expression of the antibody gene and the third drug resistance gene on a single mRNA is enabled, said expression vectors constituting a single-chain antibody library having a repertory of at least $10^{11}$;
    step (e) displaying a single chain antibody comprising VH and VL regions obtained by shuffling on the surface of a phage; and
    selecting said hosts through use of the third drug resistance gene, wherein the selected hosts comprise the recombined expression vectors.

2. A method for preparing a single chain antibody library as described in claim 1 wherein the cDNA library is selected from the group consisting of a peripheral blood cDNA library, a spleen cDNA library and a bone narrow cDNA library.

3. A method for preparing a single chain antibody library as described in claim 1 wherein the cDNA library is derived from human being or mouse.

4. A method for preparing a single chain antibody library as described in claim 1 wherein PCR amplification is performed by using at least one pair of the primers whose nucleotide sequences are as represented in Seq. ID Nos. 1-48.

5. A method for preparing a single chain antibody library as described in claim 1 in which step (a) comprises:
    substep (i) of amplifying gene fragments including the CDR1 and CDR2 regions and gene fragments including the CDR3 region in the VH region of the immunoglobulin gene using a human peripheral blood cDNA library and a human spleen cDNA library as template, wherein the CDR1 and CDR2 regions are amplified using a first primer set and the CDR3 region is amplified using a second primer set, the first primer set comprising a sequence selected from Seq. ID Nos. 1-7 and a sequence comprising Seq. ID No. 8 or 9, and the second primer set comprising a sequence of Seq. ID No. 10 or 11 and a sequence selected from Seq. ID No. 12-17;
    substep (ii) of amplifying gene fragments including the CDR1 and CDR2 regions and gene fragments including the CDR3 region of the $V_K$ region in the immunoglobulin gene by PCR using a human peripheral blood and a spleen cDNA library as template, wherein the CDR1 and CDR2 regions are amplified using a third primer set and the CDR3 region is amplified using a fourth primer set, the third primer set comprising a sequence selected from Seq. ID Nos. 18-21 and a sequence of Seq. ID No. 22 or 23, the fourth primer set comprising a sequence of Seq. ID No. 24 or 25 and a sequence selected from Seq. ID No. 26-29; and
    substep (iii) of amplifying gene fragments including the CDR1 and CDR2 regions and gene fragments including the CDR3 region of the Vγ region in the immunoglobulin gene using a human peripheral blood cDNA library or a spleen cDNA library as template, wherein the CDR1 and CDR2 regions are amplified using a fifth primer set and the CDR3 region is amplified using a sixth primer set, the fifth primer set comprising a sequence selected from Seq. ID Nos. 30-38 and a sequence selected from Seq. ID No. 39-42, the sixth primer set comprising a sequence selected from Seq. ID No. 43-46 and a sequence of Seq. ID No. 47 or 48.

6. A method for preparing a single chain antibody library as described in claim 5 in which step (b) further comprises:
    substep (i) shuffling the gene fragments between a first gene fragment and a second gene fragment, wherein the first gene fragment comprises the CDR1 and CDR2 regions and the second gene fragment comprises the CDR3 region in the VH region by PCR using two primers, one of which is selected from Seq. ID Nos. 1-7 and the other of which is selected from Seq. ID Nos. 12-17;
    substep (ii) shuffling the gene fragments between gene fragments including CDR1 and CDR2 and gene fragments including CDR3 in the $V_K$ region by PCR using two primers, one of which is selected from Seq. ID Nos. 18-21 and the other of which is selected from Seq. ID Nos. 26-29; and
    substep (iii) shuffling the gene fragments between gene fragments including CDR1 and CDR2 and gene fragments including CDR3 in the Vλ region of an antibody by PCR using two primers, one of which is selected from Seq. ID Nos. 30-38 and the other of which is selected from Seq. ID No. 47 or 48.

7. A method for preparing a single chain antibody library as described in claim 1 wherein the shuffling described in step (d) is performed by DNA recombination via recombinase.

8. A method for preparing a single chain antibody library as described in claim 7 wherein the recombinase is recombinase Cre or FLP recombinase.

9. A method for preparing a single chain antibody library as described in claim 1 wherein only single chain antibodies including VH and VL regions obtained by shuffling performed at step (d) are displayed on the surface of phage.

10. A method for preparing a single chain antibody library as described in claim 1 wherein one of said first and second non-expression vectors is a promoter-free vector and the other is a vector comprising a transcription termination signal located between the promoter and the VH library or VL library.

11. A method for preparing a single chain antibody library as described in claim 1 wherein the first and second non-expression vectors each comprise a mutated reverse-oriented repeat sequence obtained by mutating a wild-type reverse-oriented repeat sequence recognized by a recombinase.

12. A method for preparing a single chain antibody library as described in claim 11 wherein the mutated reverse-oriented repeat sequence obtained by mutating a wild-type reverse-oriented repeat sequence recognized by the recombinase is a mutated loxP sequence or a mutated FRT sequence.

13. A method for preparing a single chain antibody library as described in claim 12 wherein the mutated loxP sequence is lox71, lox66 or lox5171.

14. A method for preparing a single chain antibody library as described in claim 1 wherein the host selectively expresses a single chain antibody, which is bound on the surface of phage or released from the surface of phage.

15. A method for preparing a single chain antibody library as described in claim 14 wherein the host that selectively expresses the single chain antibody bound on the surface of phage is $E.\ coli$ with a supE mutation, and the host that expresses the single chain antibody released from the surface of phage is $E.\ coli$ without a supE mutation.

16. A single-chain antibody library obtained by using method as described in claim 1.

17. A method for preparing a single chain antibody library comprising:
    step (a) amplifying nucleic acid sequences comprising the CDR1 and CDR2 regions and the CDR3 region of the VH and VL region in an immunoglobulin gene by PCR using a cDNA library as a template to generate gene fragments;
    step (b) shuffling said gene fragments between a first gene fragment and a second gene fragment, wherein the first gene fragment comprises the CDR1 and CDR2 regions and the second gene fragment comprises the CDR3 region in each of the VH and VL regions to produce a VH library and a VL library;
    step (c) inserting said VH library into a first non-expression vector comprising an f1 ori and a first drug-resistance gene, and said VL library into a second non-expression vector comprising an f1 ori and a second drug-resistance gene, wherein one of said first and second non-expression vectors is a promoter-free vector comprising a third drug-resistance gene with a Shine-Dalgarno (SD) sequence and the other non-expression vector is a SD sequence-free vector and wherein the third drug resistance gene is different from the first and second drug resistance genes;
    step (d) shuffling gene fragments between the VH region in the VH library and the VL region in the VL library by introducing both the VH library-incorporated non-expression vector and VL library-incorporated non-expression vector into a host;
    step (dd) recombining the two non-expression vectors to create recombined expression vectors comprising an antibody gene whereby co-expression of the antibody gene and the third drug resistance gene on a single mRNA is enabled;
    step (e) displaying a single chain antibody comprising VH and VL regions obtained by shuffling on the surface of a phage; and
    selecting said hosts through use of the third drug resistance gene, wherein the selected hosts comprise the recombined expression vectors.

18. A method for preparing a single chain antibody library having a repertoire of at least $10^{11}$ comprising:
    step (a) amplifying nucleic acid sequences comprising the CDR1 and CDR2 regions and the CDR3 region of the VH and VL region in an immunoglobulin gene by PCR using a cDNA library as a template to generate gene fragments;
    step (b) shuffling said gene fragments between a first gene fragment and a second gene fragment, wherein the first gene fragment comprises the CDR1 and CDR2 regions and the second gene fragment comprises the CDR3 region in each of the VH and VL regions to produce a VH library and a VL library;
    step (c) inserting said VH library into a first non-expression vector selected from the group consisting of pSABccB-VH2 and pSABccB-VH3, and inserting said VL library into a second non-expression vector selected from the group consisting of is pSABccB-VL2 and pSABccB-VL2K;
    step (d) shuffling gene fragments between the VH region in the VH library and the VL region in the VL library by introducing both the VH library-incorporated non-expression vector and VL library-incorporated non-expression vector into a host;
    step (dd) recombining the two non-expression vectors to create expression vectors whereby expression of the antibody on the surface of a phage is enabled, said expression vectors constituting a single-chain antibody library having a repertory of at least $10^{11}$; and
    step (e) displaying a single chain antibody comprising VH and VL regions obtained by shuffling on the surface of a phage.

19. A method for screening for an antigen-specific antibody using a single-chain antibody library as described in claim 16.

20. A method for screening for an antigen-specific antibody as described in claim 19 comprising:
    step (a) of bringing an antigen into contact with the single-chain antibody library;
    step (b) of detecting a bond between a single-chain antibody and the antigen; and
    step (c) of identifying the single-chain antibody bound to the antigen.

21. A method for screening for an antigen-specific antibody as described in claim 19 comprising:
    step (a) of bringing an antigen into contact with the single-chain antibody library;
    step (b) of recovering a phage displaying single-chain antibodies bound to the antigen;
    step (c) of neutralizing a solution comprising the phage displaying the single-chain antibodies recovered at step (b);
    step (d) of amplifying the phage obtained at step (c) by means of $E.\ coli$ with a supE mutation;
    step (e) of bringing the antigen into contact with the phage, amplified at step (d), displaying the single-chain antibodies;
    step (f) of detecting a bond between the phage displaying single-chain antibodies and the antigen; and
    step (g) of identifying the single-chain antibodies bound to the antigen.

22. A method for preparing a single chain antibody library comprising:
    step (a) amplifying nucleic acid sequences comprising the CDR1 and CDR2 regions and the CDR3 region of the VH and VL region in an immunoglobin gene as a template to generate gene fragments;
    step (b) shuffling gene fragments between a first gene fragment and a second gene fragment, wherein the first gene fragment comprises the CDR1 and CDR2 regions and the second gene fragment comprises the CDR3 region in each of the VH and VL regions to produce a VH library and a VL library;

step (c) inserting said VH library into a first non-expression vector comprising an f1 ori and a first drug-resistance gene and said VL library into a second non-expression vector comprising an f1 ori and a second drug-resistance gene, wherein one of said first and second non-expression vectors is a promoter-free vector comprising a third drug resistance gene with a Shine-Dalgarno (SD) sequence and the other non-expression vector is a Shine-Dalgarno (SD) sequence-free vector, wherein the third drug resistance gene is different from the first and second drug resistance genes, and wherein when the first and second non-expression vectors are recombined, the gene fragments are shuffled between the VH region in the VH library and the VL region in the VL library and a single chain antibody gene comprising VH and VL regions and the third drug resistance gene can be co-expressed on a single mRNA; and step (d) introducing both the VH library-incorporated first non-expression vector and the VL library-incorporated second non-expression vector into a host.

23. A method for preparing a single chain antibody library as described in claim 22, wherein one of the VH and VL libraries is inserted downstream of a SD sequence of a promoter-free non-expressing vector and the other of the VH and VL libraries is inserted downstream of a promoter of a SD sequence-free non-expressing vector in step (c) such that the gene fragments are shuffled between the VH region in the VH library and the VL region in the VL library, and the VH region and the VL region are combined downstream of the promoter.

24. A method for preparing a single chain antibody library as described in claim 22, wherein the VH and VL libraries are inserted into said first and second non-expression vectors, wherein said first non-expression vector is a promoter-free non-expressing vector, and said second non-expression vector comprises a promoter and a transcription termination signal, wherein said promoter is located upstream of the transcription termination signal and the VH or VL library is located downstream of the transcription termination signal, the gene fragments are shuffled between the VH region and the VL region and the VH and VL regions are combined downstream of the promoter without the transcription termination signal intervened between the VH and VL regions.

25. A method for screening for an antigen-specific antibody as described in claim 19 wherein an antibody chip, an antibody filter or antibody beads to which the antigen-specific antibody library is bound is used.

26. A method for screening for an antigen-specific antibody as described in claim 20 wherein an antibody chip, an antibody filter or antibody beads to which the antigen-specific antibody library is bound is used.

27. A method for preparing stable VH and VL libraries said method comprising the steps of amplifying nucleic acid sequences comprising the CDR1 and CDR2 regions and the CDR3 region of the VH and VL region in an immunoglobulin gene by PCR using a cDNA library as a template to generate gene fragments;

shuffling said gene fragments between a first gene fragment and a second gene fragment, wherein the first gene fragment comprises the CDR1 and CDR2 regions and the second gene fragment comprises the CDR3 region in each of the VH and VL regions to produce VH and VL encoding sequences;

inserting said VH and VL encoding sequences into a first and second non-expression vectors, respectively, to generate stable VH and VL libraries, wherein said first non-expression vector is a promoter-free non-expressing vector comprising a first drug-resistance gene, f1 ori, and a third drug resistance gene with a Shine-Dalgarno (SD) sequence, and said second non-expression vector comprises a second drug-resistance gene, f1 ori, a promoter and a transcription termination signal, wherein the third drug resistance gene is different from the first and second drug resistance genes, wherein said promoter of the second non-expression vector is located upstream of the transcription termination signal and the VH or VL library is located downstream of the transcription termination signal, and wherein when the first and second non-expression vectors are recombined, the gene fragments are shuffled between the VH region in the VH library and the VL region in the VL library and a single chain antibody gene comprising VH and VL regions and the drug resistance gene can be co-expressed on a single mRNA;

shuffling gene fragments between the VH region in the VH library and the VL region in the VL library by introducing both the VH library and VL library into a host.

28. The method of claim 27 wherein the first and second non-expression vectors each contains an f1 origin of replication.

* * * * *

SEQUENCE LISTING

<160> NUMBER OF SEQ ID NOS: 55

<210> SEQ ID NO 1
<211> LENGTH: 40
<212> TYPE: DNA
<213> ORGANISM: Artificial
<220> FEATURE:
<223> OTHER INFORMATION: Description of Artificial Sequence:
      VH-Forward1(VH4For) primer

<400> SEQUENCE: 1
acgaagttat ctctcgagca ggtgcagctg caggagtcsg            40

```
<210> SEQ ID NO 2
<211> LENGTH: 39
<212> TYPE: DNA
<213> ORGANISM: Artificial
<220> FEATURE:
<223> OTHER INFORMATION: Description of Artificial Sequence:
      VH-Forward1(VH5For) primer

<400> SEQUENCE: 2
acgaagttat ctctcgagca ggtacagctg cagcagtca                              39

<210> SEQ ID NO 3
<211> LENGTH: 40
<212> TYPE: DNA
<213> ORGANISM: Artificial
<220> FEATURE:
<223> OTHER INFORMATION: Description of Artificial
      Sequence:VH-Forward1(VH6For) primer

<400> SEQUENCE: 3
acgaagttat ctctcgagca ggtgcagcta cagcagtggg                             40

<210> SEQ ID NO 4
<211> LENGTH: 39
<212> TYPE: DNA
<213> ORGANISM: Artificial
<220> FEATURE:
<223> OTHER INFORMATION: Description of Artificial
      Sequence:VH-Forward1(VH10For) primer

<400> SEQUENCE: 4
acgaagttat ctctcgagga ggtgcagctg ktggagwcy                              39

<210> SEQ ID NO 5
<211> LENGTH: 41
<212> TYPE: DNA
<213> ORGANISM: Artificial
<220> FEATURE:
<223> OTHER INFORMATION: Description of Artificial
      Sequence:VH-Forward1(VH12For) primer

<400> SEQUENCE: 5
acgaagttat ctctcgagca ggtccagctk gtrgagtctg g                           41

<210> SEQ ID NO 6
<211> LENGTH: 40
<212> TYPE: DNA
<213> ORGANISM: Artificial
<220> FEATURE:
<223> OTHER INFORMATION: Description of Artificial
      Sequence:VH-Forward1(VH14For) primer

<400> SEQUENCE: 6
acgaagttat ctctcgagca grtcaccttg aaggagtctg                             40

<210> SEQ ID NO 7
<211> LENGTH: 41
<212> TYPE: DNA
<213> ORGANISM: Artificial
<220> FEATURE:
<223> OTHER INFORMATION: Description of Artificial
      Sequence:VH-Forward1(VH22For) primer

<400> SEQUENCE: 7
acgaagttat ctctcgagca ggtgcagctg gtgsartctg g                           41

<210> SEQ ID NO 8
```

```
<211> LENGTH: 22
<212> TYPE: DNA
<213> ORGANISM: Artificial
<220> FEATURE:
<223> OTHER INFORMATION: Description of Artificial
      Sequence:VH-Reverse2(VH(FWR3)Back1) primer

<400> SEQUENCE: 8
acagtaatay acggccgtgt cc                                              22

<210> SEQ ID NO 9
<211> LENGTH: 22
<212> TYPE: DNA
<213> ORGANISM: Artificial
<220> FEATURE:
<223> OTHER INFORMATION: Description of Artificial
      Sequence:VH-Reverse2(VH(FWR3)Back2) primer

<400> SEQUENCE: 9
acagtaatac atggccrtgt cc                                              22

<210> SEQ ID NO 10
<211> LENGTH: 22
<212> TYPE: DNA
<213> ORGANISM: Artificial
<220> FEATURE:
<223> OTHER INFORMATION: Description of Artificial
      Sequence:VH-Forward2(VH(FWR3)For1) primer

<400> SEQUENCE: 10
ggacacggcc gtrtattact gt                                              22

<210> SEQ ID NO 11
<211> LENGTH: 22
<212> TYPE: DNA
<213> ORGANISM: Artificial
<220> FEATURE:
<223> OTHER INFORMATION: Description of Artificial
      Sequence:VH-Forward2(VH(FWR3)For2) primer

<400> SEQUENCE: 11
ggacayggcc atgtattact gt                                              22

<210> SEQ ID NO 12
<211> LENGTH: 44
<212> TYPE: DNA
<213> ORGANISM: Artificial
<220> FEATURE:
<223> OTHER INFORMATION: Description of Artificial
      Sequence:VH-Reverse1(VH-1R(N)) primer

<400> SEQUENCE: 12
gtctagccat ggaggccgag attgaggaga crgtgaccag ggtg                      44

<210> SEQ ID NO 13
<211> LENGTH: 44
<212> TYPE: DNA
<213> ORGANISM: Artificial
<220> FEATURE:
<223> OTHER INFORMATION: Description of Artificial
      Sequence:VH-Reverse1(VH-2R(N)) primer

<400> SEQUENCE: 13
gtctagccat ggaggccgag attgaggaga cggtgaccag ggtt                      44

<210> SEQ ID NO 14
<211> LENGTH: 43
<212> TYPE: DNA
```

```
<213> ORGANISM: Artificial
<220> FEATURE:
<223> OTHER INFORMATION: Description of Artificial Sequence:
      VH-Reverse1(VH-3R(N)) primer

<400> SEQUENCE: 14
gtctagccat ggaggccgag attgaagaga cggtgaccat tgt                    43

<210> SEQ ID NO 15
<211> LENGTH: 45
<212> TYPE: DNA
<213> ORGANISM: Artificial
<220> FEATURE:
<223> OTHER INFORMATION: Description of Artificial Sequence:
      VH-Reverse1(VH-4R(N)) primer

<400> SEQUENCE: 15
gtctagccat ggaggccgag attgaggaga cggtgaccgt ggtcc                  45

<210> SEQ ID NO 16
<211> LENGTH: 42
<212> TYPE: DNA
<213> ORGANISM: Artificial
<220> FEATURE:
<223> OTHER INFORMATION: Description of Artificial
      Sequence:VH-Reverse1(VH-5R(N)) primer

<400> SEQUENCE: 16
gtctagccat ggaggccgag atggttgggg cggatgcact cc                     42

<210> SEQ ID NO 17
<211> LENGTH: 43
<212> TYPE: DNA
<213> ORGANISM: Artificial
<220> FEATURE:
<223> OTHER INFORMATION: Description of Artificial
      Sequence:VH-Reverse1(VH-6R(N)) primer

<400> SEQUENCE: 17
gtctagccat ggaggccgag atsgatgggc ccttggtgga rgc                    43

<210> SEQ ID NO 18
<211> LENGTH: 50
<212> TYPE: DNA
<213> ORGANISM: Artificial
<220> FEATURE:
<223> OTHER INFORMATION: Description of Artificial
      Sequence:Vkappa-Forward1(Vkappa-1F) primer

<400> SEQUENCE: 18
ataagaatgg cccagccggc catggccgac atccrgdtga cccagtctcc             50

<210> SEQ ID NO 19
<211> LENGTH: 50
<212> TYPE: DNA
<213> ORGANISM: Artificial
<220> FEATURE:
<223> OTHER INFORMATION: Description of Artificial
      Sequence:Vkappa-Forward1(Vkappa-2F) primer

<400> SEQUENCE: 19
ataagaatgg cccagccggc catggccgaa attgtrwtga crcagtctcc             50

<210> SEQ ID NO 20
<211> LENGTH: 50
<212> TYPE: DNA
<213> ORGANISM: Artificial
<220> FEATURE:
```

```
<223> OTHER INFORMATION: Description of Artificial
      Sequence:Vkappa-Forward1(Vkappa-3F) primer

<400> SEQUENCE: 20
ataagaatgg cccagccggc catggccgat attgtgmtga cbcagwctcc          50

<210> SEQ ID NO 21
<211> LENGTH: 49
<212> TYPE: DNA
<213> ORGANISM: Artificial
<220> FEATURE:
<223> OTHER INFORMATION: Description of Artificial
      Sequence:Vkappa-Forward1(Vkappa-4F) primer

<400> SEQUENCE: 21
ataagaatgg cccagccggc catggccgaa acgacactca cgcagtctc           49

<210> SEQ ID NO 22
<211> LENGTH: 24
<212> TYPE: DNA
<213> ORGANISM: Artificial
<220> FEATURE:
<223> OTHER INFORMATION: Description of Artificial
      Sequence:Vkappa-Reverse2(VK(FWR3)Back1) primer
<220> FEATURE:
<221> NAME/KEY: misc_feature
<222> LOCATION: (16)..(16)
<223> OTHER INFORMATION: n is a, c, g, or t

<400> SEQUENCE: 22
atcytcagsy tscasncwrc tgat                                      24

<210> SEQ ID NO 23
<211> LENGTH: 24
<212> TYPE: DNA
<213> ORGANISM: Artificial
<220> FEATURE:
<223> OTHER INFORMATION: Description of Artificial
      Sequence:Vkappa-Reverse2(VK(FWR3)Back2) primer
<220> FEATURE:
<221> NAME/KEY: misc_feature
<222> LOCATION: (16)..(16)
<223> OTHER INFORMATION: n is a, c, g, or t

<400> SEQUENCE: 23
atcytcagsy tscasncwat tgat                                      24

<210> SEQ ID NO 24
<211> LENGTH: 24
<212> TYPE: DNA
<213> ORGANISM: Artificial
<220> FEATURE:
<223> OTHER INFORMATION: Description of Artificial
      Sequence:Vkappa-Forward2(VK(FWR3)For1) primer
<220> FEATURE:
<221> NAME/KEY: misc_feature
<222> LOCATION: (9)..(9)
<223> OTHER INFORMATION: n is a, c, g, or t

<400> SEQUENCE: 24
atcagywgns tgsarsctga rgat                                      24

<210> SEQ ID NO 25
<211> LENGTH: 24
<212> TYPE: DNA
<213> ORGANISM: Artificial
<220> FEATURE:
<223> OTHER INFORMATION: Description of Artificial Sequence:
      Vkappa-Forward2(VK(FWR3)For2  primer
<220> FEATURE:
```

```
<221> NAME/KEY: misc_feature
<222> LOCATION: (9)..(9)
<223> OTHER INFORMATION: n is a, c, g, or t

<400> SEQUENCE: 25
atcaatwgns tgsarsctga rgat                                           24

<210> SEQ ID NO 26
<211> LENGTH: 36
<212> TYPE: DNA
<213> ORGANISM: Artificial
<220> FEATURE:
<223> OTHER INFORMATION: Description of Artificial
      Sequence:Vkappa-Reverse1(VK1Back) primer

<400> SEQUENCE: 26
acgaagttat gtcgactttg atttccacct tggtcc                              36

<210> SEQ ID NO 27
<211> LENGTH: 36
<212> TYPE: DNA
<213> ORGANISM: Artificial
<220> FEATURE:
<223> OTHER INFORMATION: Description of Artificial
      Sequence:Vkappa-Reverse1(VK2/4Back) primer

<400> SEQUENCE: 27
acgaagttat gtcgactttg atctccasct tggtcc                              36

<210> SEQ ID NO 28
<211> LENGTH: 35
<212> TYPE: DNA
<213> ORGANISM: Artificial
<220> FEATURE:
<223> OTHER INFORMATION: Description of Artificial
      Sequence:Vkappa-Reverse1(VK3Back) primer

<400> SEQUENCE: 28
acgaagttat gtcgactttg atatccactt tggtc                               35

<210> SEQ ID NO 29
<211> LENGTH: 36
<212> TYPE: DNA
<213> ORGANISM: Artificial
<220> FEATURE:
<223> OTHER INFORMATION: Description of Artificial
      Sequence:Vkappa-Reverse1(VK5Back) primer

<400> SEQUENCE: 29
acgaagttat gtcgactttn atctccagtc gtgtcc                              36

<210> SEQ ID NO 30
<211> LENGTH: 50
<212> TYPE: DNA
<213> ORGANISM: Artificial
<220> FEATURE:
<223> OTHER INFORMATION: Description of Artificial
      Sequence:Vlambda-Forward1(Vlambda-1F) primer

<400> SEQUENCE: 30
ataagaatgg cccagccggc catggcccag tctgtsbtga cgcagccgcc               50

<210> SEQ ID NO 31
<211> LENGTH: 49
<212> TYPE: DNA
<213> ORGANISM: Artificial
<220> FEATURE:
<223> OTHER INFORMATION: Description of Artificial Sequence:
```

-continued

Vlambda-Forward1(Vlambda-2F) primer

<400> SEQUENCE: 31
ataagaatgg cccagccggc catggcctcc tatgwgctga cwcagccac        49

<210> SEQ ID NO 32
<211> LENGTH: 50
<212> TYPE: DNA
<213> ORGANISM: Artificial
<220> FEATURE:
<223> OTHER INFORMATION: Description of Artificial
      Sequence:Vlambda-Forward1(Vlambda-3F) primer

<400> SEQUENCE: 32
ataagaatgg cccagccggc catggcctcc tatgagctga yrcagcyacc       50

<210> SEQ ID NO 33
<211> LENGTH: 47
<212> TYPE: DNA
<213> ORGANISM: Artificial
<220> FEATURE:
<223> OTHER INFORMATION: Description of Artificial
      Sequence:Vlambda-Forward1(Vlambda-4F) primer

<400> SEQUENCE: 33
ataagaatgg cccagccggc catggcccag cctgtgctga ctcaryc          47

<210> SEQ ID NO 34
<211> LENGTH: 50
<212> TYPE: DNA
<213> ORGANISM: Artificial
<220> FEATURE:
<223> OTHER INFORMATION: Description of Artificial
      Sequence:Vlambda-Forward1(Vlambda-5F) primer

<400> SEQUENCE: 34
ataagaatgg cccagccggc catggcccag dctgtggtga cycaggagcc       50

<210> SEQ ID NO 35
<211> LENGTH: 50
<212> TYPE: DNA
<213> ORGANISM: Artificial
<220> FEATURE:
<223> OTHER INFORMATION: Description of Artificial
      Sequence:Vlambda-Forward1(Vlambda-6F) primer

<400> SEQUENCE: 35
ataagaatgg cccagccggc catggcccag ccwgkgctga ctcagccmcc       50

<210> SEQ ID NO 36
<211> LENGTH: 50
<212> TYPE: DNA
<213> ORGANISM: Artificial
<220> FEATURE:
<223> OTHER INFORMATION: Description of Artificial
      Sequence:Vlambda-Forward1(Vlambda-7F) primer

<400> SEQUENCE: 36
ataagaatgg cccagccggc catggcctcc tctgagctga stcaggascc       50

<210> SEQ ID NO 37
<211> LENGTH: 48
<212> TYPE: DNA
<213> ORGANISM: Artificial
<220> FEATURE:
<223> OTHER INFORMATION: Description of Artificial
      Sequence:Vlambda-Forward1(Vlambda-8F) primer

```
<400> SEQUENCE: 37
ataagaatgg cccagccggc catggcccag tctgyyctga ytcagcct        48

<210> SEQ ID NO 38
<211> LENGTH: 49
<212> TYPE: DNA
<213> ORGANISM: Artificial
<220> FEATURE:
<223> OTHER INFORMATION: Description of Artificial
      Sequence:Vlambda-Forward1(Vlambda-9F) primer

<400> SEQUENCE: 38
ataagaatgg cccagccggc catggccaat tttatgctga ctcagcccc       49

<210> SEQ ID NO 39
<211> LENGTH: 21
<212> TYPE: DNA
<213> ORGANISM: Artificial
<220> FEATURE:
<223> OTHER INFORMATION: Description of Artificial
      Sequence:Vlambda-Reverse2(VL(FWR3)Back1) primer

<400> SEQUENCE: 39
acagtaatag tcagcctcrt c                                     21

<210> SEQ ID NO 40
<211> LENGTH: 21
<212> TYPE: DNA
<213> ORGANISM: Artificial
<220> FEATURE:
<223> OTHER INFORMATION: Description of Artificial Sequence:
      Vlambda-Reverse2(VL(FWR3)Back2) primer

<400> SEQUENCE: 40
acagtaataa tcagattcat c                                     21

<210> SEQ ID NO 41
<211> LENGTH: 21
<212> TYPE: DNA
<213> ORGANISM: Artificial
<220> FEATURE:
<223> OTHER INFORMATION: Description of Artificial
      Sequence:Vlambda-Reverse2(VL(FWR3)Back3) primer

<400> SEQUENCE: 41
acaatgatac tcagcctcat c                                     21

<210> SEQ ID NO 42
<211> LENGTH: 21
<212> TYPE: DNA
<213> ORGANISM: Artificial
<220> FEATURE:
<223> OTHER INFORMATION: Description of Artificial
      Sequence:Vlambda-Reverse2(VL(FWR3)Back4) primer

<400> SEQUENCE: 42
acagtggtag tcactctcat c                                     21

<210> SEQ ID NO 43
<211> LENGTH: 21
<212> TYPE: DNA
<213> ORGANISM: Artificial
<220> FEATURE:
<223> OTHER INFORMATION: Description of Artificial
      Sequence:Vlambda-Forward2(VL(FWR3)For1) primer

<400> SEQUENCE: 43
```

```
gaygaggctg actattactg t                                          21
```

<210> SEQ ID NO 44
<211> LENGTH: 21
<212> TYPE: DNA
<213> ORGANISM: Artificial
<220> FEATURE:
<223> OTHER INFORMATION: Description of Artificial
      Sequence:Vlambda-Forward2(VL(FWR3)For2) primer

<400> SEQUENCE: 44

```
gatgaatctg attattactg t                                          21
```

<210> SEQ ID NO 45
<211> LENGTH: 21
<212> TYPE: DNA
<213> ORGANISM: Artificial
<220> FEATURE:
<223> OTHER INFORMATION: Description of Artificial
      Sequence:Vlambda-Forward2(VL(FWR3)For3) primer

<400> SEQUENCE: 45

```
gatgaggctg agtatcattg t                                          21
```

<210> SEQ ID NO 46
<211> LENGTH: 21
<212> TYPE: DNA
<213> ORGANISM: Artificial
<220> FEATURE:
<223> OTHER INFORMATION: Description of Artificial
      Sequence:Vlambda-Forward2(VL(FWR3)For4) primer

<400> SEQUENCE: 46

```
gatgagagtg actaccactg t                                          21
```

<210> SEQ ID NO 47
<211> LENGTH: 36
<212> TYPE: DNA
<213> ORGANISM: Artificial
<220> FEATURE:
<223> OTHER INFORMATION: Description of Artificial
      Sequence:Vlambda-Reverse1(VL1/2Back) primer

<400> SEQUENCE: 47

```
acgaagttat gtcgactagg acggtsasct tggtcc                          36
```

<210> SEQ ID NO 48
<211> LENGTH: 36
<212> TYPE: DNA
<213> ORGANISM: Artificial
<220> FEATURE:
<223> OTHER INFORMATION: Description of Artificial
      Sequence:Vlambda-Reverse1(VL7Back) primer

<400> SEQUENCE: 48

```
acgaagttat gtcgacgagg acggtcagct gggtgc                          36
```

<210> SEQ ID NO 49
<211> LENGTH: 27
<212> TYPE: DNA
<213> ORGANISM: Artificial
<220> FEATURE:
<223> OTHER INFORMATION: Description of Artificial
      an artificially synthesized primer sequence

<400> SEQUENCE: 49

```
cgtgaaaaaa ttattattcg caattcc                                    27
```

```
<210> SEQ ID NO 50
<211> LENGTH: 24
<212> TYPE: DNA
<213> ORGANISM: Artificial
<220> FEATURE:
<223> OTHER INFORMATION: Description of Artificial
      an artificially synthesized primer sequence

<400> SEQUENCE: 50
acgcggttcc agcggatccg gata                                            24

<210> SEQ ID NO 51
<211> LENGTH: 20
<212> TYPE: PRT
<213> ORGANISM: Homo sapiens

<400> SEQUENCE: 51

Thr Arg Val Thr Ser Phe Leu Asp Trp Ile His Glu Gln Met Glu Arg
1               5                   10                  15

Asp Leu Lys Thr
            20

<210> SEQ ID NO 52
<211> LENGTH: 20
<212> TYPE: PRT
<213> ORGANISM: Homo sapiens

<400> SEQUENCE: 52

Pro Ala Pro Ser His Leu Val Glu Lys Ile Val Tyr His Ser Lys Tyr
1               5                   10                  15

Lys Pro Lys Arg
            20

<210> SEQ ID NO 53
<211> LENGTH: 257
<212> TYPE: PRT
<213> ORGANISM: Artificial
<220> FEATURE:
<223> OTHER INFORMATION: Description of Artificial
      sequence: peptide (TM1 scFv) from E. coli

<400> SEQUENCE: 53

Glu Thr Thr Leu Thr Gln Ser Pro Ser Ser Leu Ser Ala Ser Val Gly
1               5                   10                  15

Asp Arg Val Thr Ile Thr Cys Arg Thr Ser Gln Thr Ile Asn Asn Tyr
            20                  25                  30

Leu Asn Trp Tyr Gln Gln Lys Pro Gly Lys Ala Pro Lys Val Leu Ile
        35                  40                  45

Phe Gly Ala Ser Arg Leu Gln Ser Gly Val Pro Ser Arg Phe Ser Gly
    50                  55                  60

Ser Gly Ser Gly Thr His Phe Thr Leu Thr Ile Thr Ser Leu Gln Pro
65                  70                  75                  80

Glu Asp Val Ala Thr Tyr Tyr Cys Gln Gln Ser Tyr Gly Thr Pro Tyr
                85                  90                  95

Thr Phe Gly Gln Gly Thr Lys Val Glu Ile Lys Val Asp Ile Thr Ser
            100                 105                 110

Tyr Asn Val Tyr Tyr Thr Lys Leu Ser Leu Glu Gln Val Gln Leu Gln
        115                 120                 125

Gln Trp Gly Ala Gly Leu Leu Lys Pro Ser Glu Thr Leu Ser Leu Thr
    130                 135                 140

Cys Ala Ile Tyr Asn Gly Ser Phe Gly Gly Tyr Tyr Trp Asn Trp Ile
```

```
                145                 150                 155                 160
Arg Gln Pro Pro Gly Lys Gly Leu Glu Trp Ile Gly Glu Ile Asn Gln
                    165                 170                 175

Arg Glu Ser Thr Asn Phe Asn Pro Ser Phe Lys Ser Arg Val Thr Met
                180                 185                 190

Ser Val Asp Thr Ser Asn Asn Gln Phe Ser Leu Arg Leu Ser Ser Leu
            195                 200                 205

Thr Ala Ala Asp Thr Ala Val Tyr Phe Cys Ala Arg Gly Leu Tyr Tyr
        210                 215                 220

Asp Thr Thr Gly Phe Phe Asp Ala Phe Ala Val Trp Gly Gln Gly Thr
225                 230                 235                 240

Thr Val Thr Val Ser His Leu Gly Leu Met Gly His His His His His
                    245                 250                 255

His

<210> SEQ ID NO 54
<211> LENGTH: 95
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 55
<211> LENGTH: 97
<212> TYPE: PRT
<213> ORGANISM: Homo sapiens

<400> SEQUENCE: 55

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```